US 11,417,509 B2

(12) United States Patent
Pandurangan et al.

(10) Patent No.: US 11,417,509 B2
(45) Date of Patent: *Aug. 16, 2022

(54) CURRENT DETECTION DEVICE AND SPECTROMETER USING IHE SAME

(71) Applicant: ATONARP INC., Tokyo (JP)

(72) Inventors: Anand Pandurangan, San Jose, CA (US); Siva Selvaraj, San Jose, CA (US); Anoop Hegde, Milpitas, CA (US); Prakash Sreedhar Murthy, Tokyo (JP)

(73) Assignee: ATONARP INC., Tokyo (JP)

( * ) Notice: Subject to any disclaimer, the term of this patent is extended or adjusted under 35 U.S.C. 154(b) by 59 days.

This patent is subject to a terminal disclaimer.

(21) Appl. No.: 16/621,356

(22) PCT Filed: Jul. 19, 2018

(86) PCT No.: PCT/JP2018/026999
§ 371 (c)(1),
(2) Date: Dec. 11, 2019

(87) PCT Pub. No.: WO2019/017413
PCT Pub. Date: Jan. 24, 2019

(65) Prior Publication Data
US 2021/0143000 A1    May 13, 2021

Related U.S. Application Data

(63) Continuation-in-part of application No. 15/656,909, filed on Jul. 21, 2017, now Pat. No. 10,224,192.

(51) Int. Cl.
*H01J 49/42* (2006.01)
*H01J 49/02* (2006.01)
(Continued)

(52) U.S. Cl.
CPC ...... *H01J 49/4215* (2013.01); *H01J 49/0013* (2013.01); *H01J 49/022* (2013.01); *A61B 5/0075* (2013.01)

(58) Field of Classification Search
CPC .. H01J 49/0013; H01J 49/022; H01J 49/4215; A61B 5/0075; G01R 19/12; G01R 29/12
See application file for complete search history.

(56) References Cited

U.S. PATENT DOCUMENTS 6,243,034 B1 * 6/2001 Regier ................. H03M 1/145
341/155
6,614,286 B1 * 9/2003 Tang ...................... G06G 7/184
327/337
(Continued)

FOREIGN PATENT DOCUMENTS

EP    0880821 A1    12/1998
JP    05264352 A  * 10/1993
(Continued)

OTHER PUBLICATIONS

International Search Report (PCT/ISA/210) dated Oct. 2, 2018, by the Japanese Patent Office as the International Searching Authority for International Application No. PCT/JP2018/02699.
(Continued)

*Primary Examiner* — David E Smith
(74) *Attorney, Agent, or Firm* — Buchanan Ingersoll & Rooney PC

(57) ABSTRACT

A device of detecting a current from a sensor is disclosed. The device includes an integrating circuit including a network of capacitors for providing a gain setting and configured to convert the current to a voltage ramp over a length of integration time, the integrating circuit further including a reset switch configured to connect an input and an output of the network of capacitors; an ADC configured to digitize the voltage ramp into a plurality of voltage samples; and a
(Continued)

set of modules including an analyzing module configured to analyze the plurality of voltage samples to determine a slope of the voltage ramp; an outputting module configured to determine a magnitude of the current based on the slope of the voltage ramp and the gain setting; and a reconfiguring module that is configured to reconfigure the network of capacitors and reset the voltage ramp via the reset switch.

20 Claims, 10 Drawing Sheets

(51) Int. Cl.
*A61B 5/00* (2006.01)
*H01J 49/00* (2006.01)

(56) References Cited

U.S. PATENT DOCUMENTS

| | | | |
|---|---|---|---|
| 6,809,313 B1 | 10/2004 | Gresham et al. | |
| 6,847,036 B1 | 1/2005 | Darling et al. | |
| 10,224,192 B2 * | 3/2019 | Pandurangan | H01J 49/08 |
| 2005/0077897 A1 | 4/2005 | Syms | |
| 2007/0215814 A1 | 9/2007 | Kitchen | |
| 2009/0045816 A1 * | 2/2009 | Robinson | G01R 29/24 |
| | | | 324/457 |
| 2009/0121151 A1 * | 5/2009 | Denton | H01J 49/025 |
| | | | 250/397 |
| 2013/0332099 A1 * | 12/2013 | Lai | G01R 19/0053 |
| | | | 702/104 |
| 2014/0048683 A1 | 2/2014 | Soh et al. | |
| 2014/0209811 A1 * | 7/2014 | Chou | G01T 1/185 |
| | | | 250/374 |
| 2015/0129756 A1 | 5/2015 | Fitzgerald | |

FOREIGN PATENT DOCUMENTS

| | | |
|---|---|---|
| JP | H05264352 A | 10/1993 |
| WO | 9610164 A1 | 4/1996 |
| WO | 97-07591 A1 | 2/1997 |
| WO | 03019206 A1 | 3/2003 |
| WO | 2007118186 A2 | 10/2007 |

OTHER PUBLICATIONS

Written Opinion (PCT/ISA/237) dated Oct. 2, 2018, by the Japanese Patent Office as the International Searching Authority for International Application No. PCT/JP2018/026999.

The extended European Search Report dated Mar. 9, 2021, by the European Patent Office in corresponding European Application No. 18835524.2. (11 pages).

* cited by examiner

[Fig. 1]
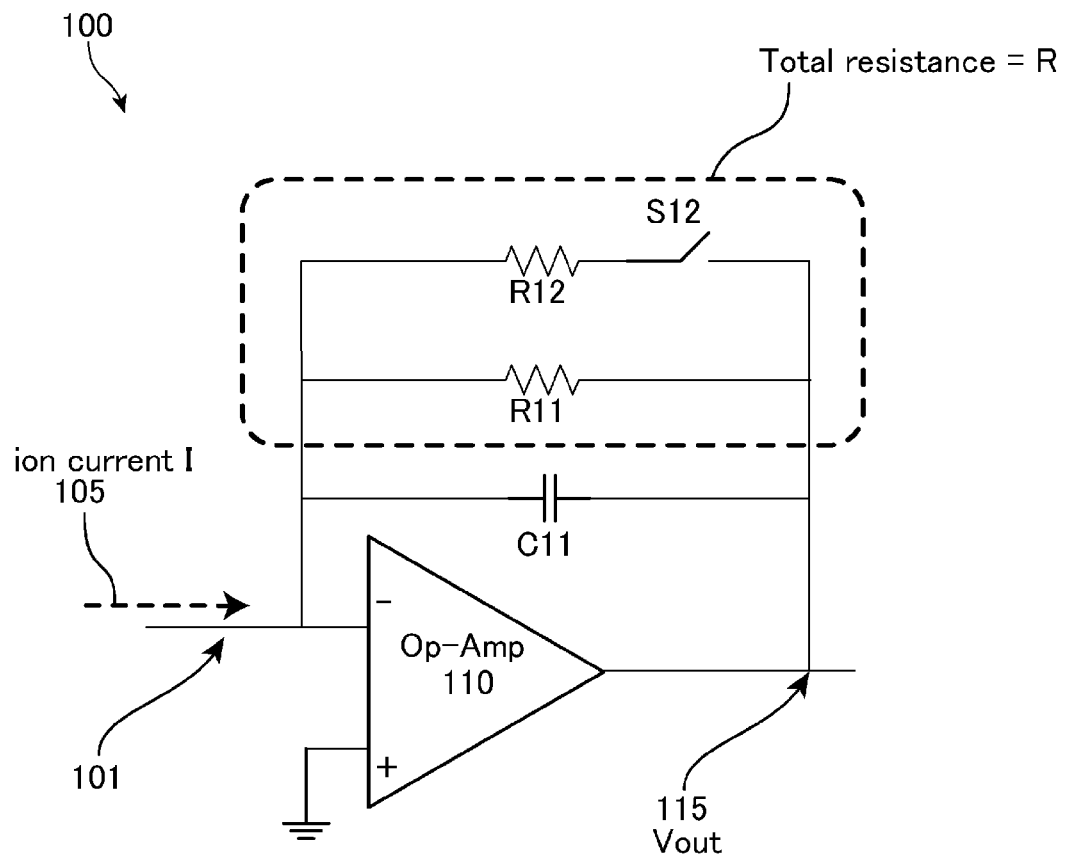
(PRIOR ART)

[Fig. 2]
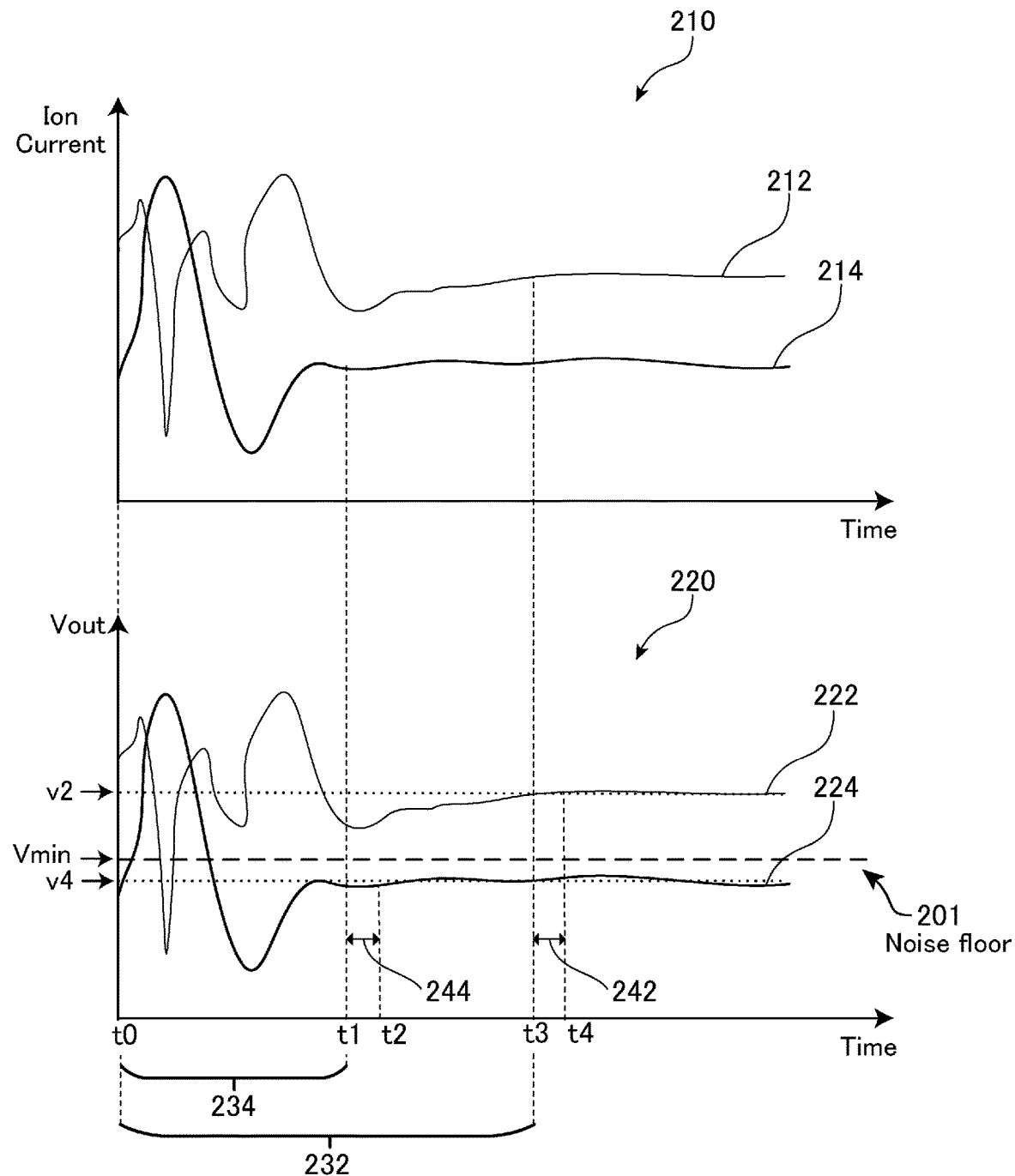
(PRIOR ART)

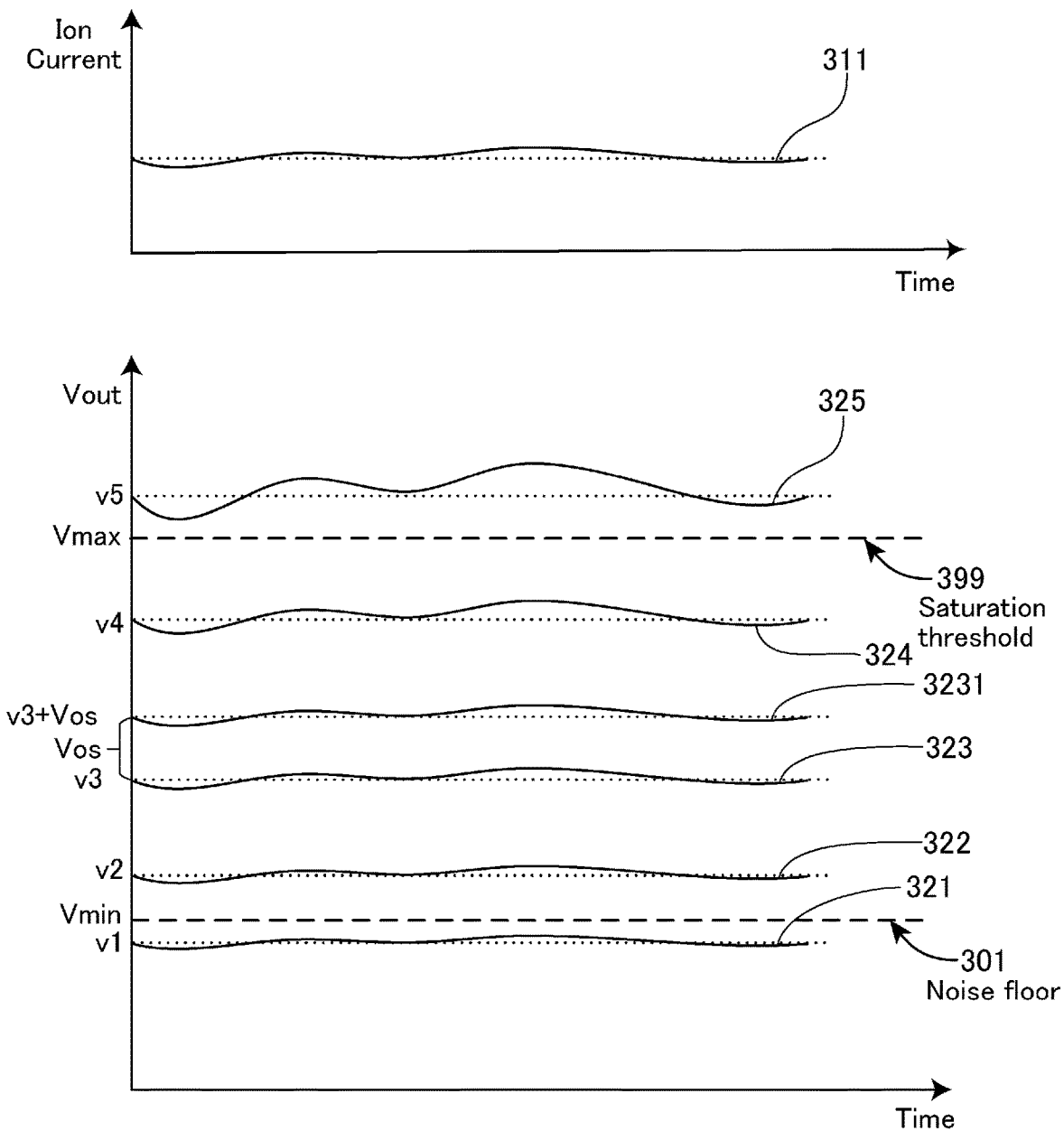
[Fig. 3]
(PRIOR ART)

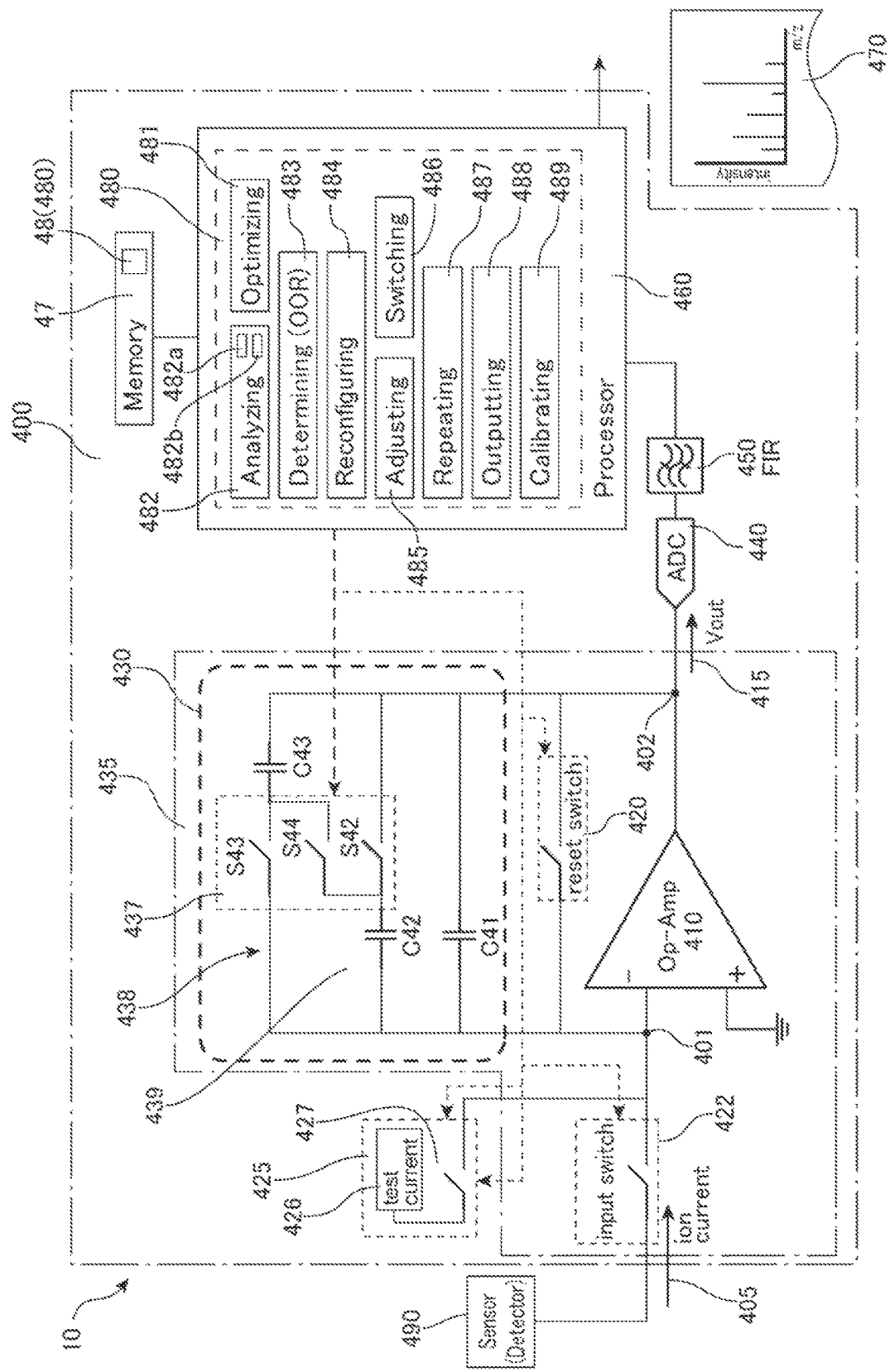
[Fig. 4]

[Fig. 5]
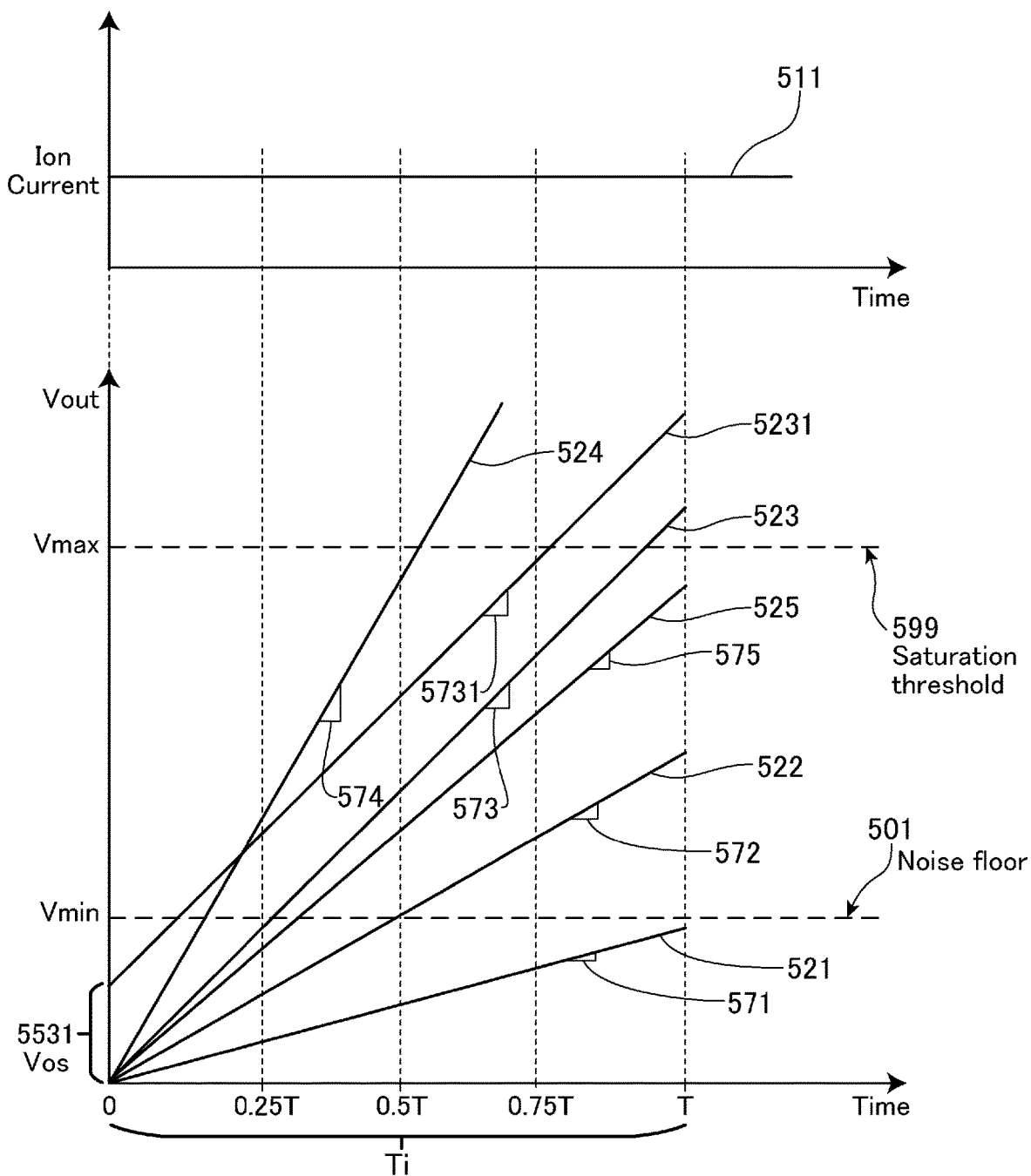

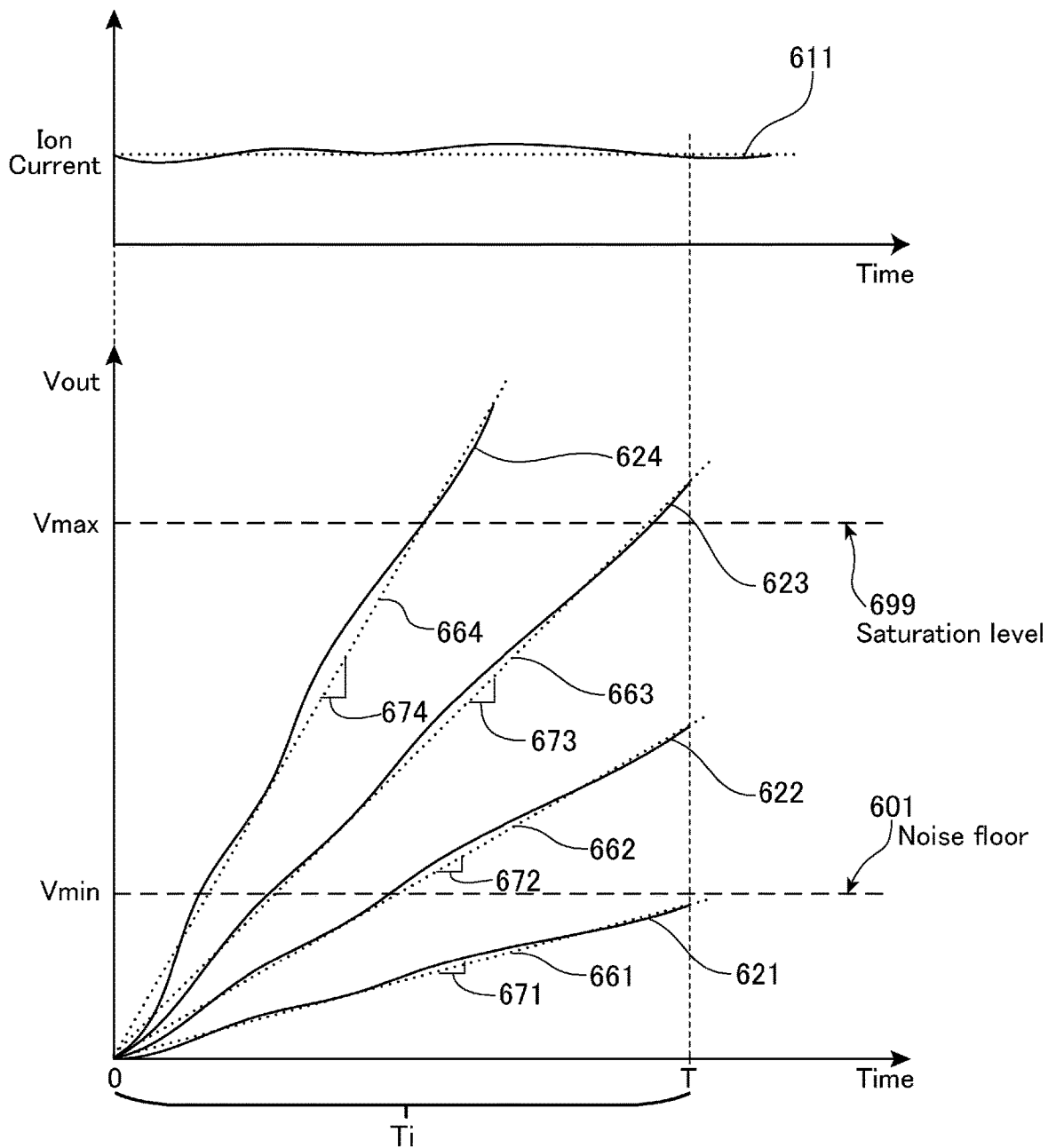
[Fig. 6]

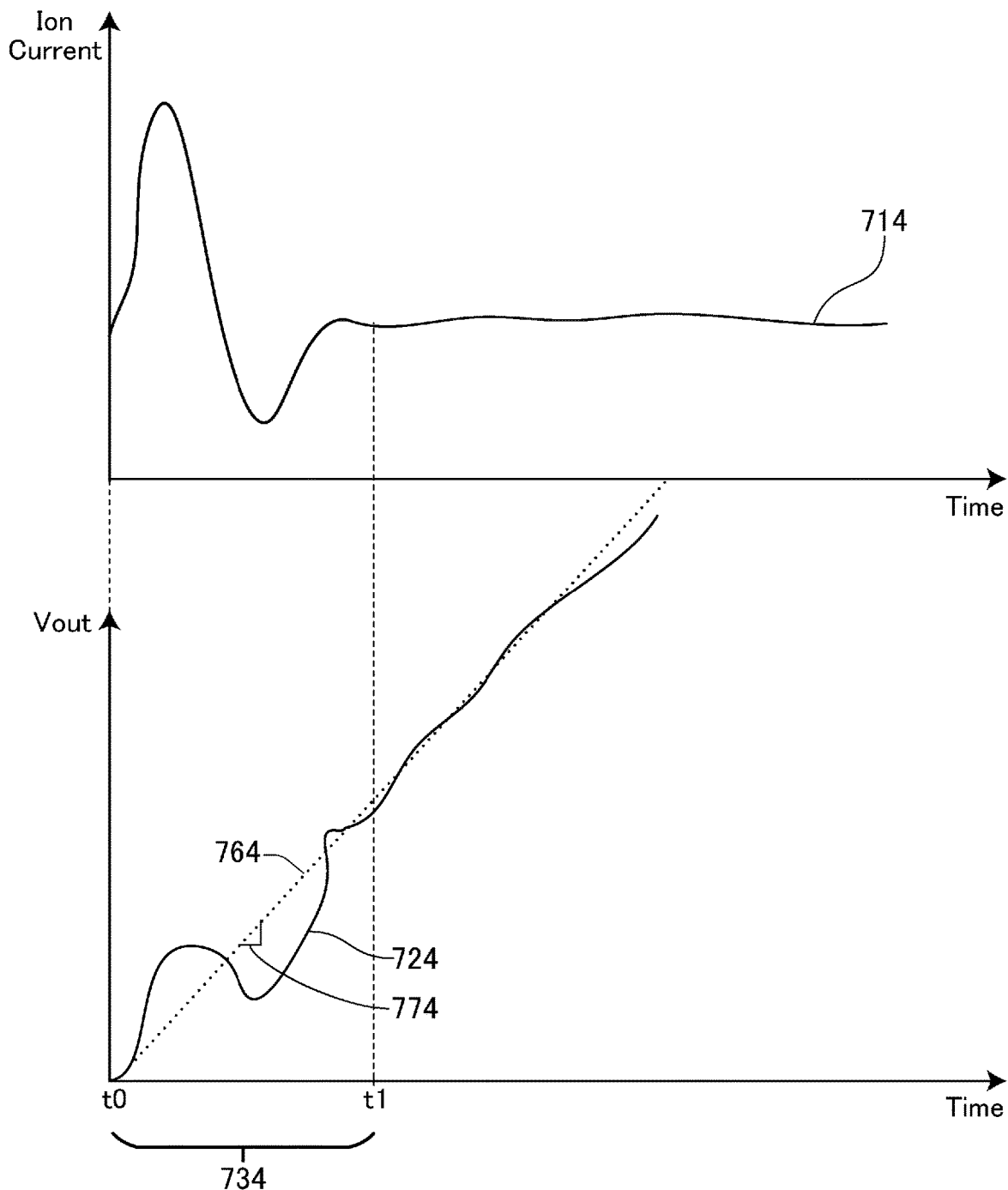

[Fig. 8]
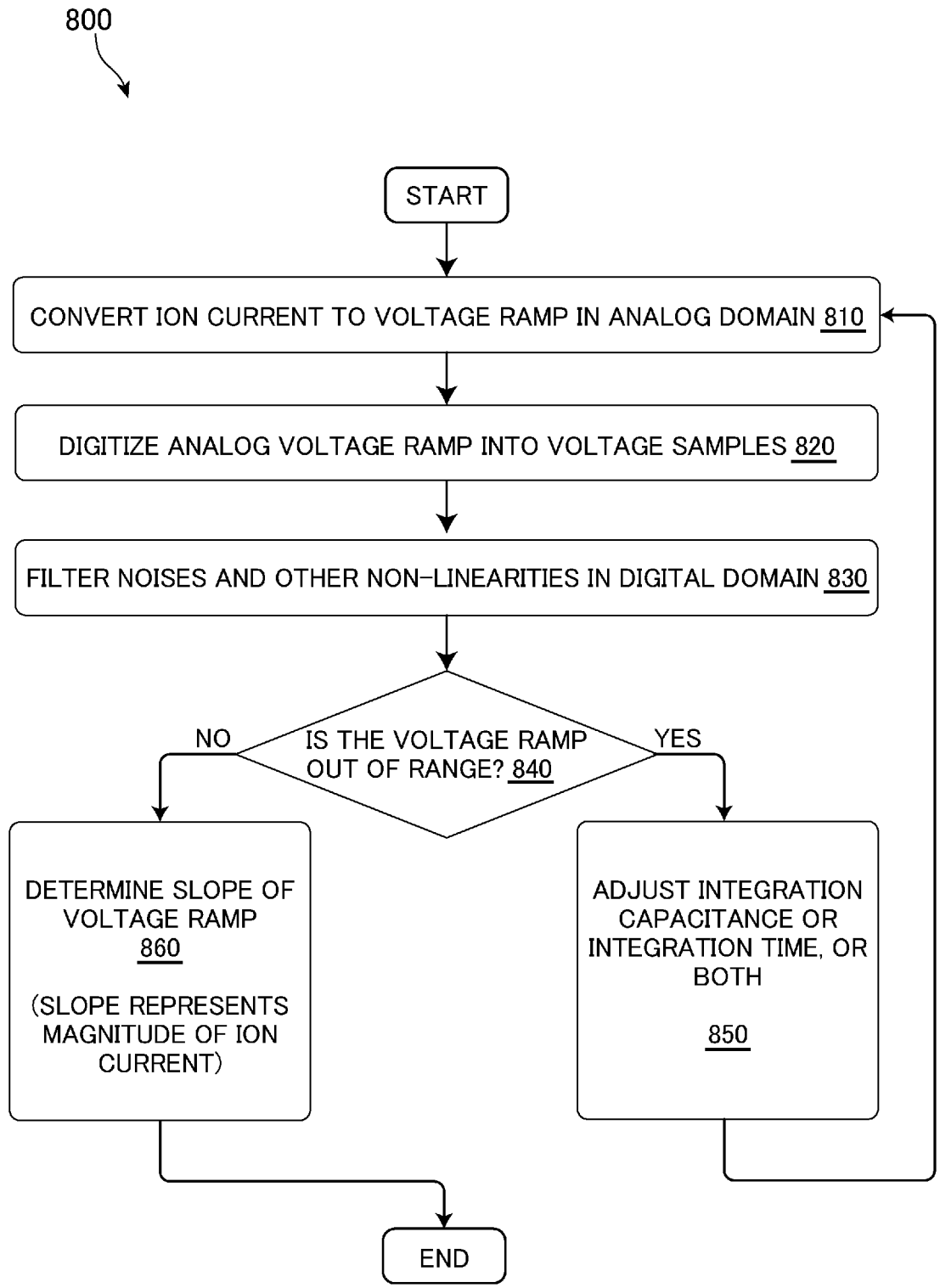

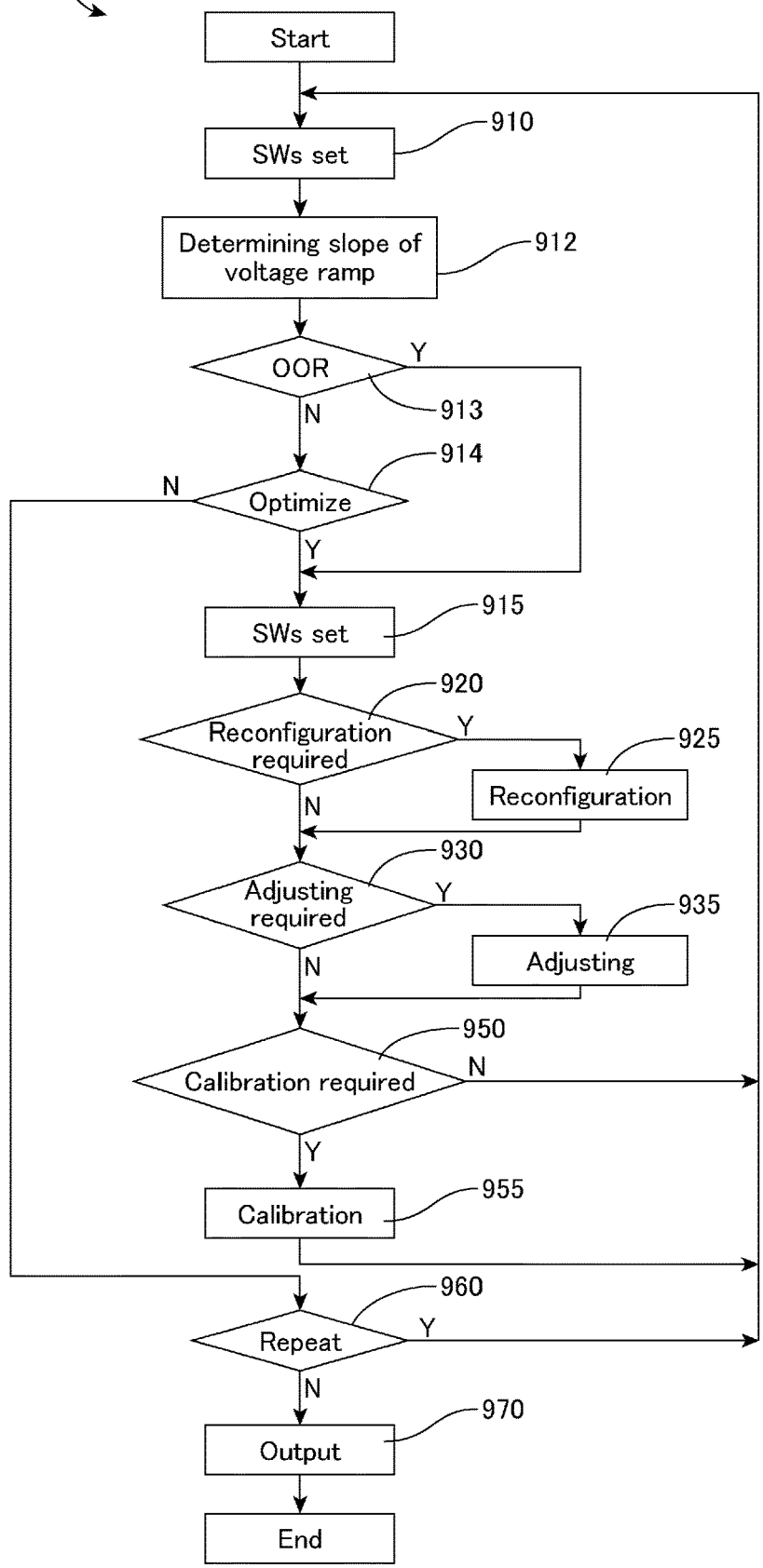

[Fig. 10]
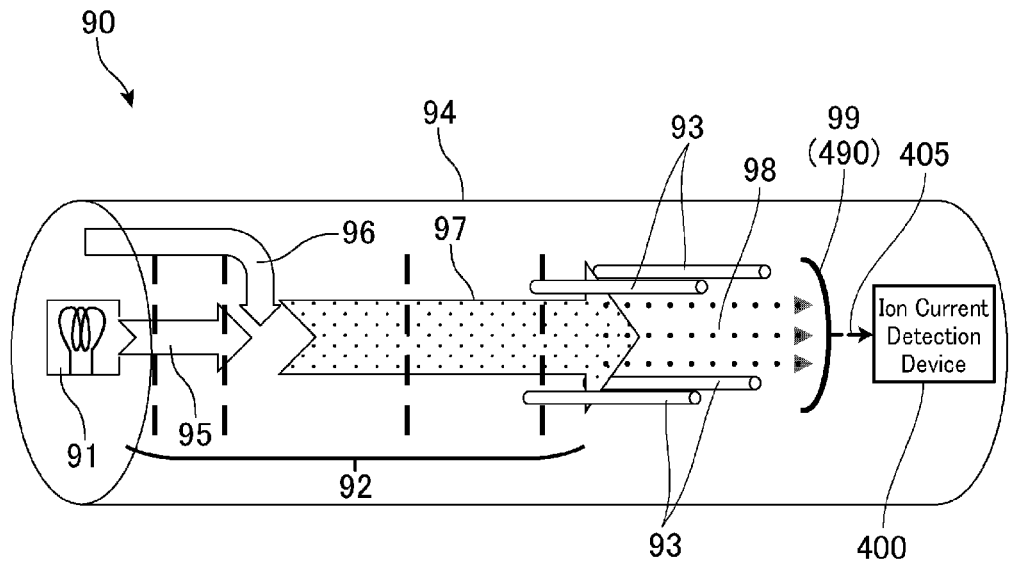
[Fig. 11]
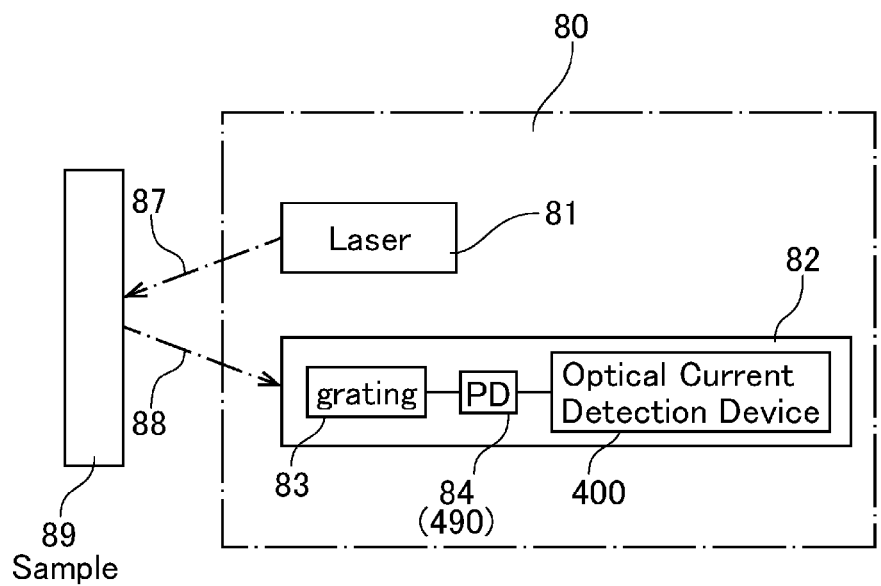

CURRENT DETECTION DEVICE AND SPECTROMETER USING THE SAME

TECHNICAL FIELD

The present disclosure generally relates to a high-speed low-noise current detection device and a spectrometer such as a mass spectrometer, optical spectrometer and the like using the device.

BACKGROUND ART

A spectrometer is a scientific instrument used to separate and measure spectral components of a physical phenomenon. A spectrometer may include a sensor that measures a continuous variable of a phenomenon where the spectral components are somehow mixed. For instance, in the optical filed, a spectrometer (an optical spectrometer) may separate and measure individual narrow bands of light in such as color, frequency, wave length and the like called a spectrum, while a mass spectrometer measures the spectrum of the masses of the atoms or molecules present in a gas. Spectrometers were developed in early studies of physics, astronomy, and chemistry, but are applied to industrial uses such as in quantitative analysis not only in qualitative analysis. Some type of sensors employed in spectrometers outputs a current corresponding to the intensity and/or quantity of the object to be measured, a device that detects a current from the sensor is required in such spectrometers for measuring, determining or interpreting the output of the sensor.

A challenging problem encountered in design and implementation of a spectrometer, among others, resides in how the detection device or circuit can accurately and efficiently detect the current, which may vary over a large dynamic range. Depending on the amount of the specimen and the relative concentration or intensity of a specific kind of specimen, for example, in a miniaturized, portable or battery-driven type spectrometer, a current may be as large as 100 nano-ampere (nA), or $10^{-7}$ A, and as small as 10 femto-ampere (fA), or $10^{-14}$ A. Namely, a dynamic range of the current may be as large as seven orders of magnitude, if not more. The detection device thus needs to be capable of detecting currents over this large dynamic range, which readily imposes a stringent design requirement. On top of that, detecting a minute current in the fA range imposes another stringent design requirement. Electronic circuits are subjected to various kinds of noise sources in the system they are designed to serve. However, the detection circuit using an op-amp that has a very high open-loop gain typically suffers from a higher noise and a long recovery time from saturation.

Accordingly, there remains a need for a device and a method to overcome the aforementioned problems and drawbacks and enable to provide high-speed and low-noise detection device and method.

SUMMARY OF INVENTION

One of aspects of this invention is a device of detecting a current from a sensor. The device comprises an integrating circuit including a network of capacitors for providing a gain setting and configured to convert the current to a voltage ramp over a length of integration time. The integrating circuit further includes a reset switch configured to connect an input and an output of the network of capacitors when the reset switch is turned on. The device further comprises an analog-to-digital converter (ADC) configured to digitize the voltage ramp into a plurality of voltage samples, and a set of modules. The set of modules includes an analyzing module that is configured to analyze the plurality of voltage samples to determine a slope of the voltage ramp; an outputting module that is configured to determine a magnitude of the current based on the slope of the voltage ramp and the gain setting; and a reconfiguring module that is configured to reconfigure the network of capacitors and reset the voltage ramp via the reset switch.

The set of modules may further include a determining module that is configured to determine an out-of-range (OOR) state based on the voltage ramp. The reconfiguring module may reconfigure the network of capacitors according to the OOR state. The determining module may predict the OOR state based on the voltage ramp and a predetermined detectable range. The set of modules may include an adjusting module to adjust the length of integration time according to the OOR state. The reconfiguring module may reconfigure the network of capacitors to adjust the length of integration time to improve a detection speed or a detection accuracy.

The analyzing module may include a module configured to determine a first-order fitting line based on the plurality of voltage samples and a module configured to designate a slope of the first-order fitting line as the slope of the voltage ramp.

The integrating circuit may include an input switch configured to turn on and off the current to the network of capacitors. The set of modules may include a switch controlling module that is configured to control the input switch to pass the current while the current is converted to the voltage ramp and to block the current while the reset switch is turned on to reset the voltage ramp.

The set of modules may include a repeating module that is configured to repeat converting of the current to the voltage ramp for multiple times. The plurality of voltage samples may comprise multiple sets of voltage samples resulted from the repeating. The analyzing modules may determine the slope of the voltage ramp by averaging over the multiple sets of voltage samples. The set of modules may include a calibrating module that is configured to calibrate the gain setting of the integrating circuit by sending a calibrating current of a known value to the integrating circuit and recording the slope of the voltage ramp resulted from the calibrating current.

The device may include one or more digital filters configured to reduce a noise component of the plurality of voltage samples and generate the one or more voltage samples of the plurality of voltage samples. The device may include a memory (memory medium) that stores the set of modules, and a processor that executes the set of modules.

Another aspect of this invention is a mass spectrometer. The mass spectrometer may include an ion drive configured to ionize gas molecules into an ion flow comprising a plurality of gas ions having a plurality of values of atomic mass unit (AMU); a mass filter configured to selectively pass a first part of the plurality of gas ions, each gas ion of the first part of the plurality of gas ions having a first value of AMU; an ion sensor configured to sense the first part of the plurality of gas ions and generate a first ion current; and the device that detects the first ion current.

Yet another aspect of this invention is an optical spectrometer. The optical spectrometer may include an optical sensor configured to measure properties of light over a specific portion of the electromagnetic spectrum and generate a first optical current, and the device that detects the first optical current.

Yet another aspect of this invention is a system that includes a sensor configured to generate a current signal to be interpreted and the device for detecting the current signal.

Yet another aspect of this invention is a method of detecting a current from a sensor using a device. The device includes an integrating circuit including a network of capacitors for providing a gain setting and a reset switch for connecting an input and an output of the network of capacitors, an analog-to-digital converter (ADC), and a processor. The method includes: (i) converting, over a length of integration time, the current to a voltage ramp by the integrating circuit having a gain setting; (ii) digitizing, by the ADC, the voltage ramp into a plurality of voltage samples, the plurality of voltage samples representing the voltage ramp; (iii) analyzing, by the processor, the plurality of voltage samples to determine the slope of the voltage ramp; (iv) determining a magnitude of the current based on the slope of the voltage ramp and the gain setting; and (v) reconfiguring the network of capacitors to reset the voltage ramp via the reset switch.

The method may include determining an out-of-range (OOR) state based on the voltage ramp. The step of reconfiguring may include reconfiguring the network of capacitors according to the OOR state. The step of determining the OOR state may include predicting the OOR state based on the voltage ramp and a predetermined detectable range. The method may include adjusting the length of integration time according to the OOR state. The step of reconfiguring may include reconfiguring the network of capacitors to adjust the length of integration time to improve a detection speed or a detection accuracy.

The step of analyzing may comprise determining a first-order fitting line based on the plurality of voltage samples, and designating a slope of the first-order fitting line as the slope of the voltage ramp.

The method may include switching the input switch to pass the current while the current is converted to the voltage ramp and to block the current while the reset switch is turned on to reset the voltage ramp. The method may include repeating converting of the current to the voltage ramp for multiple times, wherein the plurality of voltage samples comprise multiple sets of voltage samples and determining the slope of the voltage ramp by averaging over the multiple sets of voltage samples.

Yet another aspect of this invention is a computer program (program product) for a computer to operate a system that includes a spectrometer. The spectrometer includes a sensor and a device configured to detect a current from the sensor. The computer program includes executable codes for performing steps of (a) analyzing the plurality of voltage samples to determine a slope of the voltage ramp; (b) determining a magnitude of the current based on the slope of the voltage ramp and the gain setting; and (c) reconfiguring the network of capacitors to reset the voltage ramp via the reset switch based on the slope of the voltage ramp. The program (program product) may be supplied with stored in a memory medium.

The device and the system for detecting a current provide means for realizing high-speed and low-noise detection for the current. The improved current detection scheme according to the present invention is able to greatly improve performances of a spectrometer and other system equipped with the device.

BRIEF DESCRIPTION OF DRAWINGS

Non-limiting and non-exhaustive embodiments of the present disclosure are described with reference to the following figures, wherein like reference numerals refer to like parts throughout the various figures unless otherwise specified:

FIG. 1 is a diagram depicting a traditional ion current detection circuit implementable in a mass spectrometer;

FIG. 2 is a diagram depicting input and output waveforms of a traditional ion current detection circuit;

FIG. 3 is a diagram depicting waveforms of various gain settings of a traditional ion current detection circuit;

FIG. 4 is a diagram depicting an example current detecting device in accordance with an embodiment of the present disclosure;

FIG. 5 is a diagram depicting a set of waveforms of various gain settings of an example ion current detecting device in accordance with an embodiment of the present disclosure;

FIG. 6 is a diagram depicting another set of waveforms of various gain settings of an example ion current detecting device in accordance with an embodiment of the present disclosure;

FIG. 7 is a diagram depicting input and output waveforms of an example ion current detecting device in accordance with an embodiment of the present disclosure;

FIG. 8 is a flowchart of an example process of current detection in accordance with an embodiment of the present disclosure;

FIG. 9 is a flowchart of an example method of current detection using the current detection device;

FIG. 10 is a diagram depicting an example mass spectrometer in accordance with an embodiment of the present disclosure; and FIG. 11 is a diagram depicting an example spectrometer in accordance with an embodiment of the present disclosure.

DESCRIPTION OF EMBODIMENTS

In the following description, reference is made to the accompanying drawings that form a part thereof, and in which is shown by way of illustrating specific exemplary embodiments in which the disclosure may be practiced. These embodiments are described in sufficient detail to enable those skilled in the art to practice the concepts disclosed herein, and it is to be understood that modifications to the various disclosed embodiments may be made, and other embodiments may be utilized, without departing from the scope of the present disclosure. The following detailed description is, therefore, not to be taken in a limiting sense.

A mass spectrometer is an instrument used in an analytical technique of mass spectrometry to analyze a composition of a sample material or a chemical specimen. Mass spectrometry is able to measure or otherwise determine, at least, relative concentrations of components (such as atoms and/or molecules) that form the specimen. The specimen, typically in gas form, is ionized by a flow of high-energy electrons, transforming atoms and/or molecules of the specimen into various kinds of ions. Each kind of the ions may have a specific mass-to-charge ratio (hereinafter "m/z"). The ionized specimen (hereinafter "ion flow") is then accelerated electrically to enter into a filter, which passes only some ions (hereinafter the "selected ions") in the ion flow that exhibit certain m/z, while blocking others. The selected ions, after passing the filter, arrive at an electrode, where charges carried by the selected ions are collected and form a current (hereinafter "ion current") that flows to a detection circuit/subsystem. The detection circuit measures the ion current, and designates a magnitude of the ion current as a representation of an abundance of a certain kind of atoms and/or molecules associated with passing ions. One of typical filter is a quadrupole mass filter (QMF). The m/z of the ions that are passable by a QMF is typically determined by one or more radio-frequency (RF) and/or direct-current (DC) voltages applied to the QMF. The mass spectrometer is configured to adjust the RF and DC voltages of the QMF, thereby changing the passible ions from ions of a specific m/z to ions of a different m/z. With this process repeated for different m/z values, the relative concentrations of atoms and/or molecules that form the specimen can be revealed. The filter may be realized by other types of filters such as a Wien filter, a time-of-flight (TOF) analyzer, an ion trap, and the like.

A challenging problem encountered in design and implementation of a mass spectrometer, among others, resides in how the detection circuit can accurately and efficiently detect the ion current, which may vary over a large dynamic range. Depending on the amount of the specimen (measured in, for example, numbers of mole) and the relative concentration of a specific kind of ion in the specimen, an ion current may be as large as 100 nano-ampere (nA), or $10^{-7}$ A, and as small as 10 femto-ampere (fA), or $10^{-14}$ A. Namely, a dynamic range of the ion current may be as large as seven orders of magnitude, if not more. The detection circuit thus needs to be capable of detecting ion currents over this large dynamic range, which readily imposes a stringent design requirement. On top of that, detecting a minute current in the fA range imposes another stringent design requirement. Electronic circuits are subjected to various kinds of noise sources in the system they are designed to serve, and this is especially true for a mass spectrometer. At least the generation of the high-energy electron flow, the ionization of the gas specimen, the acceleration of the ion flow and the operation of the QMF all employ high-voltage, high-power and/or high-frequency oscillating voltage sources. These voltages sources could easily couple electrical noise to the sensitive detection circuits, disturbing the electrical signals therein and affecting the measurement result.

FIG. 1 depicts a schematic diagram of an ion current detection circuit 100 that is commonly used in a mass spectrometer. The detection circuit 100 includes an operational amplifier (op-amp) 110, a positive input terminal of which is connected to electrical ground. A feedback capacitor C11 is provided for feedback stability of detection circuit 100, the value of which is typically in the range of 10 femto-farad (fF) to 100 fF. The capacitor C11 is connected between an output terminal of op-amp 110 and a negative input terminal of op-amp 110. Resistors R11 and R12 are gain resistors. While the resistor R11 is fixedly connected in parallel with the capacitor C11, the resistor R12 is configured to connect in parallel with the capacitor C11 and the resistor R11 when a switch S12 is closed or otherwise turned on. When the switch S12 is open or otherwise turned off, the resistor R12 is not electrically connected with the detection circuit 100 and thus does not participate in the operation of detection circuit 100. An ion current 105 that is collected on a collecting electrode of the mass spectrometer flows into the detection circuit 100 through an input node 101, and through the resistor R11 (and the resistor R12 if the switch S12 is on). While flowing through the resistors R11 and R12, the ion current 105 is converted into an output voltage (hereinafter "Vout") 115. Specifically, with R representing the total resistance between the output terminal and the negative input terminal of op-amp 110, and I representing a magnitude of ion current 105, the detection circuit 100 would generate an output voltage Vout (Vout=I·R). Namely, Vout is proportional to I with a gain of R, and thus represents or otherwise corresponds to the magnitude of ion current 105. Alternatively speaking, the ion current 105 can be back calculated as I (I=Vout/R), and interpreted as an indication of an abundance of a specific kind of ion or molecule in a specimen being analyzed by the mass spectrometer. The gain of R is programmable through the switch S12, thereby providing various gain settings of detection circuit 100. For example, when S12 is open, R=R11. When S12 is closed, R=R11//R12 (the composite resistance of R11 in parallel with R12). The different gain settings may be useful for different levels of ion current 105. For example, a weaker ion current 105 may require a larger gain setting, while a stronger ion current 105 may do fine with a smaller gain setting.

In practical applications, the detection circuit 100 of FIG. 1 suffers numerous limitations. First of all, it is difficult for the detection circuit 100 to accurately detect a weak ion current 105. Apparently, it is not possible to detect an arbitrarily infinitesimal signal. In general, for any electronic detection circuit, there exist various sources of noise and circuit offsets that collectively determine a minimum detectable level of the detection circuit, or "noise floor", below which the detection circuit is not able to distinguish a signal intended to be detected from the noise the circuit is susceptible to. That is, when the noise floor is higher than the signal to be detected, the signal is "buried" under the noise floor and cannot be detected by the circuit. The detection circuit 100 realized in discrete electronic components typically has a noise floor of 300 micro-volts (uV) or so. With a gain setting practically limited to $6e^9$ (that is, 6,000,000,000) or so, the noise floor of 300 uV limits the smallest detectable ion current to be around 50 fA for the detection circuit 100. That is, the detection circuit 100 may not be able to detect ion current 105 if the ion current 105 is around or below 50 fA. Using a gain setting higher than $6e^9$ would require a gain resistor that may be too large to fit into a miniaturized mass spectrometer, and/or the high-value gain resistor may need to have a larger error in resistance value, not to mention that a high-value gain resistor would become a major noise source in the detection circuit 100 and significantly raise the noise floor. Thus, using a gain resistor of a higher value may not only fail to extend the detectable range of detection circuit 100 below 50 fA, but actually reversely impact the minimum detectable current level of detection circuit 100. In practical situations, however, a high-performance mass spectrometer is often required to detect an ion current as low as 10 fA or so. The detection circuit 100 is thus not able to meet the requirement.

Secondly, the detection circuit 100 often suffers a slow detection process due to a long waiting period in practical detection situations. Each of waiting periods 232 and 234 shown in FIG. 2 is an example of the long waiting period, with the waiting period 232 longer than the waiting period 234. FIG. 2 shows a graph 210, of the ion current 105, and a graph 220, of Vout 115, for the detection circuit 100 of FIG. 1. Specifically, the graph 210 shows two ion current waveforms, 212 and 214, while graph 220 shows two Vout waveforms, 222 and 224. When the ion current 105 of waveform 212 is received at the input node 101, a corresponding Vout of waveform 222 is generated at the output terminal of op-amp 110. Similarly, when the ion current 105 of waveform 214 is received at the input node 101, a corresponding Vout of waveform 224 is generated at the output terminal of op-amp 110. Each set of ion current and Vout waveforms may represent ions of a respective m/z. That is, the waveforms 212 and 222 may result from ions of a specific value of m/z, while the waveforms 214 and 224 may result from ions of a different value of m/z.

The reason for a possible long waiting period of detection circuit 100, as implemented in a mass spectrometer, is explained below. When the QMF is adjusted from passing ions of a first value of m/z (hereinafter "$(m/z)_1$") to passing ions of a second value of m/z, (hereinafter "$(m/z)_2$"), the transition normally results in a transient or temporary perturbation to the ion current caused by capacitive coupling from various sources in the mass spectrometer, and is often manifested as one or more large peaks or valleys, or both, in the waveform of the ion current. A measurement of the ion current during this transitional phase of peaks and valleys may result in an erroneous reading of the actual ion current of $(m/z)_2$. To get an accurate measurement of the $(m/z)_2$ ion current, the detection circuit of the mass spectrometer may need to wait until this temporary perturbation has settled. This waiting period for the ion current to settle may be a hundred times longer, or even more, than the actual measurement time after the ion current has settled. The long waiting period, during which the ion current detection would not yield representative results, drastically slows down the process of ion current detection in the mass spectrometer.

This phenomenon is clearly shown in FIG. 2, wherein each of ion current waveforms 212 and 214 and each of Vout waveforms 222 and 224 shows an initial period of peaks and valleys. For example, the QMF of the mass spectrometer may have just changed from $(m/z)_1$ to $(m/z)_2$ at time t0, resulting in the waveform 212 and waveform 222 which represent the corresponding ion current 105 and Vout 115, respectively. The waveform 212 and waveform 222 have a shape similar to one another, as they are related by the gain of R as defined in the linear equation of Vout=I·R, as previously presented. Each of the waveforms 212 and 222 exhibits relatively large peaks and valleys between the times t0 and t3, and does not settle until time t3. Consequently, the detection circuit 100 would need to wait for a waiting period 232, which has a length of (t3~t0), before giving a representative value, v2, of the ion current of $(m/z)_2$. The actual detection time for the representative value v2 is shown as a detection period 242, which has a length of (t4~t3). Similarly, the QMF of the mass spectrometer may have just changed from a third value of m/z, (hereinafter "$(m/z)_3$") to a fourth value of m/z, (hereinafter "$(m/z)_4$") at time t0, resulting in the waveform 214 and waveform 224 which represent the corresponding ion current 105 and Vout 115, respectively. The waveform 214 and waveform 224 also have a similar shape to one another, as they are also related by the gain of R as defined in the linear equation of Vout=I·R. Each of the waveforms 214 and 224 exhibits relatively large peaks and valleys between times t0 and t1, and does not settle until time t1. Consequently, the detection circuit 100 would need to wait for a waiting period 234, which has a length of (t1–t0), before giving a representative value, v4, of the ion current of $(m/z)_4$. The actual detection time for the representative value v4 is shown as a detection period 244, which has a length of (t2–t1). Typically, the detection periods 242 and 244, usually of a few milliseconds, may have a same length, which is deterministic by the design of the detection circuit. In contrast, the waiting periods 232 and 234 may have different lengths, which tend to be less controlled or otherwise less predictable, and usually in the range of tens even hundreds of milliseconds. That is, most of the time for the ion current detection of the spectrometer is consumed by the waiting periods 232 and 234, instead of by the actual detection periods 242 and 244.

It is worth noting that in each of the graphs 210 and 220 of FIG. 2, the time axis is normalized with respect to the time when an adjustment is made to the QMF of the mass spectrometer to pass ions of a different m/z value. That is, for the waveforms 212 and 222, t0 represents the time when a QMF setting is changed from $(m/z)_1$ to $(m/z)_2$. Likewise, for the waveforms 214 and 224, t0 represents the time when a QMF setting is changed from $(m/z)_3$ to $(m/z)_4$. Since a mass spectrometer typically has only one QMF, the waveforms 212 and 222 cannot be generated at the same time as the waveforms 214 and 224. The two sets of waveforms need to be generated separately at two distinctive points in time, or in "two distinctive scans" of the sample specimen. Therefore, the waveforms 212 and 214 ought not to be interpreted as happening concurrently, and the waveforms 222 and 224 ought not to be interpreted as happening concurrently.

It is also worth noting that a noise floor 201 of the detection circuit 100 is shown in the graph 220 of FIG. 2. As discussed previously, a Vout 115 of a value lower than the noise floor 201 will not be detected by the detection circuit 100. Take a waveform 224 for example. The waveform 224 may be detectable for some time during the waiting period 234, as the waveform 224 is higher than the noise floor 201 corresponding to a value Vmin, for a portion of waiting period 234. However, the waveform 224 is completely below the noise floor 201 after settling at t1, and thus undetectable. Namely, while the detection circuit 100 is supposed to detect the representative value of v4 for Vout 115 during the detection period 244, in reality the detection circuit 100 is not able to detect the value v4, given the fact that v4 is below Vmin. Instead, the detection circuit 100 would detect Vout 115 as simply 0 volt.

When the detection circuit 100 detects Vout 115 to be very small or close to 0, the detection circuit 100 may attempt to increase a gain setting of the detection circuit 100 to see if a larger Vout 115 can be resulted. As mentioned previously, the gain setting of the detection circuit 100 is determined by the total resistance R between the output terminal and the negative input terminal of op-amp 110. By increasing the total resistance R between the output terminal and the negative input terminal of op-amp 110, a higher gain will be applied to ion current 105, and a higher Vout 115 will be resulted, which may thus become higher than the noise floor 201 and become detectable by the detection circuit 100.

FIG. 3 shows various waveforms of Vout 115 that correspond to a same waveform 311 of the ion current 105 under various gain settings (i.e., various values of R) of the detection circuit 100. Governed by the linear equation of Vout=I·R, as previously discussed, a higher gain setting results in a higher value of Vout 115. That is, a waveform 322 corresponds to a higher R value than a waveform 321, while a waveform 323 corresponds to a higher R value than the waveform 322. Likewise, the waveform 323 corresponds to a higher R value than the waveform 322, and a waveform 324 corresponds to a higher R value than the waveform 323, whereas a waveform 325 corresponds to a higher R value than the waveform 324.

It is worth noting that, among the waveforms 321-325 of FIG. 3, only the waveforms 322, 323 and 324 are detectable by the detection circuit 100. As discussed above, the waveform 321 is undetectable, since the waveform 321 corresponds to a Vout of value v1 that is below the noise floor 301 of value Vmin. In addition, the waveform 325 is also undetectable, and that is because the waveform 325 corresponds to a Vout of value v5 that is above the saturation threshold 399 of value Vmax. A saturation threshold 399 of value Vmax represents a maximal detectable voltage of Vout 115 for the detection circuit 100. When Vout 115 is above Vmax, the circuit 100 may saturate and thus not function as desired (e.g., the high open-loop gain of op-amp 110 may no longer be maintained), and the linear relationship of Vout=I·R between Vout 115 and the ion current 105 may not be truthfully maintained. Namely, when Vout 115 is detected to be at or above Vmax, the back calculation of I=Vout/R may no longer be valid. Both the waveforms 321 and 325 are referred to as "out of range", or "OOR" in short, as they are out of the detectable range of Vout within which the detection circuit 100 is designed to work properly.

A way for the detection circuit 100 to move a waveform from a state of OOR into the detectable range between Vmin and Vmax is by changing the gain setting R of the detection circuit 100. For example, Vout 115 may move from the waveform 321 to any of the waveforms 322, 323 and 324 by increasing the total resistance R between the output terminal and the negative input terminal of op-amp 110. Similarly, Vout 115 may move from the waveform 325 to any of the waveforms 322, 323 and 324 by decreasing the total resistance R between the output terminal and the negative input terminal of op-amp 110. The total resistance R may be decreased or increased by turning on or off switch S12 of FIG. 1. The change of resistance R, however, gives rise to another limitation of the detection circuit 100: it is a slow process for the detection circuit 100 to move from a gain setting to a different gain setting. Specifically, to provide a high gain for detecting weak ion current in the fA range, the detection circuit 100 is required to use high value resistors, such as R1 and R2 of FIG. 1. The high value resistors would result in large time constants for the detection circuit 100, making changing the gain setting a slow process. For example, it may take hundreds of milliseconds for Vout 115 to settle after the detection circuit 100 changes the gain setting.

For the same reason, the detection circuit 100 is slow to respond to a sudden surge in the ion current 105. In the practical operation of a mass spectrometer, occasionally there may be a dramatically high concentration of certain ions in the ion flow. The high concentration of ions may pass the QMF, causing a temporarily high level of ion current 105, or a "sudden surge". The sudden surge may temporarily saturate the detection circuit 110, causing Vout 115 to enter an OOR state. Although a change in gain setting may not be required to deal with the sudden surge, as the sudden surge will eventually pass, due to the long time constants described above the detection circuit 100 would be slow in recovering from the saturation and coming out the OOR state.

In addition to the limitations stated above, there are other secondary reasons why a traditional detection circuit of a mass spectrometer, such as the detection circuit 100 of FIG. 1, suffers from high noise and low speed. For example, since the magnitude of ion current 105 is represented by the measured absolute value of Vout 115, the detection circuit 100 requires the use of op-amp 110 that has a very high open-loop gain. Op-amp 110 that exhibits a very high open-loop gain typically suffers from a higher noise and a long recovery time from saturation.

The present disclosure aims to overcome the various limitations of the traditional ion current detection circuit 100 of FIG. 1 as discussed above. Specifically, novel detection techniques will be described in the present disclosure to provide high-speed and low-noise detection circuits specifically customized for the use of ion current detection in contemporary and next-generation mass spectrometers.

FIG. 4 depicts a schematic diagram of a system 10 that includes a sensor (detector) 490 and a device 400 for detecting a current signal 405 from the sensor 490. The sensor 490 may be an ion current detector, a photo current detector and the like that is configured to generate a current signal 405 to be interpreted or measured for determining magnitudes, intensities, concentrations or quantities of an object to be measured. The high-speed and low-noise current detection device (circuit) 400 may be implemented in a mass spectrometer for detecting an ion current, in an optical spectrometer for detecting an optical current or on another spectrometer. Hereinafter, the present invention will be described by referring to a device 400 applied to a mass spectrometer as an example.

The device 400 detects an ion current 405 from an ion current detector 490. The device 400 comprises: an integrating circuit 435 including a network of capacitors 430 for providing a gain setting and configured to convert the current to a voltage ramp over a length of integration time Ti; an analog-to-digital converter (ADC) 440 configured to digitize the voltage ramp into a plurality of voltage samples; one or more digital filters 450 configured to reduce a noise component of the plurality of voltage samples and generate the one or more voltage samples of the plurality of voltage samples, a memory 47 and a processor 460. The integrating circuit 435 further includes a reset switch 420 configured to connect an input 401 and an output 402 of the network of capacitors 430 when the reset switch 420 is turned on, and an input switch 422 configured to on and off the current 405 to the network of capacitors 430. The network of capacitors includes a plurality of capacitors such as C41, C42 and C43. The network of capacitors 430 also includes a reconfiguring switch matrix 437 and a channel matrix 438 to connect the plurality of capacitors flexibly in parallel and/or serial each other and to dynamically reconfigure the connections between or among the plurality of capacitors. By the network of capacitors 430, it is possible to select an appropriate capacitance (capacity) as an integrating gain between the minimum capacitance and the maximum capacitance that can be configured by one or plurality of capacitors dynamically and in a short time, for example, in one or a few clocks or cycles.

The integrating circuit 435 may include an op-amp 410, a non-inverting terminal of which may be connected to a reference voltage. The reference voltage may be the electrical ground of the mass spectrometer for the detection device 400 having a single-ended configuration. Alternatively, the reference voltage may be a common-mode voltage, which may be electrically seen as a virtual ground, for the detection device 400 having a fully differential configuration. The reset switch 420 may connect between an output terminal 402 of op-amp 410 and an inverting terminal of op-amp 410 that is the input terminal 401 of op-amp 410. The reset switch 420 may short-circuit the output terminal 402 of op-amp 410 to the input node 401 when the reset switch 420 is closed or otherwise turned on.

The network of capacitors (a variable relay) 430 may be connected between the input terminal 401 and the output terminal 402 of op-amp 410, in parallel with the reset switch 420. The Op-amp 410, the reset switch 420 and the network of capacitors 430 may collectively be referred to as an "integrating circuit" 435 of the ion current detection device 400. The network of capacitors 430 may include a capacitor matrix 439 including capacitors C41, C42 and C43 as well as switching matrix 437 that includes switches S42, S43 and S44, and may function as a programmable or otherwise variable capacitor bank which may provide a total capacitance having a value of C between the output terminal 402 and input terminal 401 of op-amp 410. Through closing or otherwise turning on one or more of switches S42, S43 and S44, the network of capacitors 430 is reconfigured and the capacitance value C of network of capacitors 430 between the output terminal 402 and input terminal 401 of op-amp 410 may be adjusted. For example, assuming each of C41, C42 and C43 has a capacitance value of Cunit, network of capacitors 430 may present a total capacitance of C=Cunit when each of switches S42, S43 and S44 is open or otherwise turned off. When both S42 and S43 are turned off while S44 is turned on, the network of capacitors 430 may present a total capacitance of C=1.5·Cunit. When S42 is turned on and both S43 and S44 are turned off, the network of capacitors 430 may present a total capacitance of C=2·Cunit. Alternatively, with both S42 and S43 turned on and S44 turned off, the network of capacitors 430 may present a total capacitance of C=3·Cunit. As will be clarified below, the value of C of the network of capacitors 430 may determine a gain setting of the integrating circuit 435. To detect the ion current 405 having a dynamic range as wide as seven orders of magnitude, the network of capacitors 430 may provide a large range of gain settings through various on-off combinations of switches S42, S43 and S44 to reconfigure the capacitors network to program the total capacitance C of the network of capacitors 430. The switching matrix 437 including switches S42, S43 and S44 may be referred to as "range switches" 437 for this reason.

In this embodiment, the detection device 400 includes the analog-to-digital converter (ADC) 440, one or more stages of the digital filter 450 (denoted as "FIR" in FIG. 4) and the processor 460. The ADC 440 may digitize a voltage ramp of Vout 415, which is an analog signal presented at the output terminal 402 of op-amp 410, and provide digital samples that may collectively represent the voltage ramp of Vout 415. The digital samples output by the ADC 440 may pass through the one or more stages of the digital filter 450 before being received and analyzed by the processor 460. The processor 460 may analyze the digital samples received from the digital filter 450 and subsequently adjust the gain setting of the network of capacitors 430 by reconfiguring using the switching matrix 437 and/or control the reset switch 420. The processor 460 may also determine a magnitude, a representation or otherwise a figure of merit 470 of ion current 405 based on the digital samples. More details regarding the ADC 440, the digital filter 450 and the processor 460 will be given in later parts of the present disclosure.

In some embodiments, the detection device 400 may include the input switch 422 that is controlled by the processor 460 to pass or block the ion current 405. The input switch 422 may be controlled in conjunction with the reset switch 420 to short-circuit the network of capacitors 430 during a reset operation of detection device 400. Specifically, during normal operation of the detection device 400, the processor 460 may control the reset switch 420 and the input switch 422 such that the reset switch 420 is open (i.e., turned off) and the input switch 422 is closed (i.e., turned on), so as to pass the ion current 405 through the network of capacitors 430. In contrast, during the reset operation of detection device 400, the processor 460 may control the reset switch 420 and the input switch 422 such that the reset switch 420 is closed (i.e., turned on) and the input switch 422 is open (i.e., turned off), so as to short-circuit the network of capacitors 430 and reset Vout 415 to 0. The input switch 422 being turned off prevents the ion current 405 from flowing through the reset switch 420 (which may have a none-zero on-resistance) and creating an unwanted voltage drop across the output terminal 402 and the input terminal 401 of the op-amp 410.

The integrating circuit 435, which includes the op-amp 410, the reset switch 420 and the network of capacitors 430, may integrate the ion current 405 over a period of time (integrating time) Ti and convert the ion current 405 to a voltage ramp at the output terminal 402 of the op-amp 410, presented as an output voltage Vout 415. Specifically, with C representing the total capacitance of the network of capacitors 430, I representing a magnitude of the ion current 405, and Ti representing a length of the integrating time, the integration circuit 435 may generate Vout (Vout=I·Ti/C). Namely, when presented on a two-dimensional plane with the x-axis being the integrating time Ti and the y-axis being the voltage Vout output by the op-amp 410, Vout may be presented as a linear ramp of a slope of I/C. The slope of Vout may thus be proportional to I with a gain of 1/C, and thus may represent or otherwise correspond to the magnitude of ion current 405. Alternatively speaking, the ion current 405 may be back calculated as I=Vout·C/Ti, and interpreted as an indication of an abundance of ion or molecule having a specific m/z in a specimen being analyzed by the mass spectrometer 10.

The ADC 440 may perform analog-to-digital conversion with precisely timed conversion-start pulses, with the pulses separated in time of 10 to 20 microseconds (us). The ADC 440 may be of 24 bits in structure, and may have an equivalent number of bits (ENOB) of 20 to 21.

After the ADC 440 completes a conversion for a sample of analog input, the digitized voltage samples may pass through the digital filter 450 and be received by the processor 460 for further analysis. The processor 460 may determine, based on the digitized samples of Vout 415 provided by the ADC 440 and passing through the digital filter 450, whether Vout 415 is out of a detection range of the device 400 (more details below). If the processor 460 determines that Vout 415 is outside of the detection range, the processor 460 may reconfigure the network of capacitors 430 and/or adjust the length of integrating time Ti as an effort to place Vout 415 back within the detection range of the device 400.

In this embodiment, a program (program produce, software, application) 48 stored in the memory 47 is provided for running on the host processing system (processor) 460, may provide for functioning a set of modules 480 for implementing processes, logics or analytics of the device 400 while also performing other functions. The application software 48 may be provided other memory medium readable by the processor 460 or other types of computer. The set of modules 480 may include an optimizing module 481 that is configured to optimize operating conditions for monitoring, measurement and the like; an analyzing module 482 that is configured to analyze the plurality of voltage samples to determine a slope of the voltage ramp; a determining module 483 that is configured to determine an out-of-range (OOR) state based on the voltage ramp; a reconfiguring module 484 that is configured to reconfigure the network of capacitors 430 and reset the voltage ramp via the reset switch 420 according to the slope, the OOR state and/or other optimizing conditions; an adjusting module 485 that is configured to adjust the length of integration time Ti according to the OOR state and/or other optimizing conditions; a switch controlling module 486 that is configured to control the input switch 422 and the reset switch 420; a repeating module 487 that is configured to repeat converting of the current to the voltage ramp for multiple times; an outputting module 488 that is configured to determine a magnitude of the current based on the slope of the voltage ramp and the gain setting of the network of capacitors 430; and a calibrating module 489 that is configured to calibrate the gain setting of the integrating circuit 435 by sending a calibrating current of a known value by a test current (calibrating current) output unit 426 to the integrating circuit 435 and recording the slope of the voltage ramp resulted from the calibrating current.

The analyzing module 482 may include a module 482a configured to determine a first-order fitting line based on the plurality of voltage samples, and a module 482b configured to designate a slope of the first-order fitting line as the slope of the voltage ramp. The switch controlling module 486 is configured to control the input switch 422 to pass the current 405 while the current 405 is converted to the voltage ramp and to block the current 405 while the reset switch 420 is turned on to reset the voltage ramp. The repeating module 487 is configured to repeat converting of the current 405 to the voltage ramp for multiple times, wherein the plurality of voltage samples comprise multiple sets of voltage samples resulted from the repeating, and the analyzing modules 482 determines the slope of the voltage ramp by averaging over the multiple sets of voltage.

The device 400 of FIG. 4 may be subject to a noise floor and a saturation threshold, which collectively define the detectable range of detection circuit for Vout 415. A properly chosen gain setting of the network of capacitors 430 (i.e., a properly chosen total capacitance C of the network of capacitors 430) may be needed to maintain Vout 415 within the detectable range. During the analyzing module 482 analyzes the received samples of Vout 415, the determining module 483 determines or predicts that Vout 415 is out of range, the reconfiguring module 484 may reconfigures the network of capacitors 430 to adjust the gain setting. The reconfiguring module 484 may also control or otherwise cause the reset switch 420 to turn on so as to reset the voltage ramp to bring Vout 415 back to zero before the integrating circuit 435 can integrate again to build up a new voltage ramp at Vout 415 with the new gain setting of the network of capacitors 430. The resetting of Vout 415 immediately following the gain change of the network of capacitors 430 may be crucial for fast settling of Vout 415 after the gain change. In contrast, the detection circuit 100 is not provided with a reset switch, and thus may suffer from a long settling time when the gain setting of circuit 100 is changed, as previously discussed. For comparison, the detection circuit 100 may typically take hundreds of milliseconds to settle, whereas the detection circuit 400 may typically take merely a millisecond or less to settle. Thus, with the device 400, the detection speed can be greatly improved when a change in gain setting is involved. Likewise, a sudden surge in the ion current 405, similar to the sudden surge in the ion current 105 as previously discussed for the detection circuit 100, may also be quickly settled by the operation of reset switch 420.

Electro mechanical relays may be used to discharge as the reset switch 420 and as the switching matrix 437 between integrating feedback capacitors of the network of capacitors 430. MOS relay drive mechanism may be used to control the switches that has a performance in terms of minimizing charge injection. This design using the electro mechanical relays and MOs relay drive mechanism may provide a clear opportunity for compensating the effects of any residual charge injection that actually come through.

FIG. 5 illustrates waveforms of Vout 415 resulted from the ion current 405 of a waveform 511. The ion current 405 may flow through the input node 401 of device 400 and then through the network of capacitors 430 to build up Vout 415 at the output terminal 402 of op-amp 410. The reconfigurable network of capacitors 430 may be configured to provide one of several gain settings for the detection device 400. Each gain setting, determined by the total capacitance C of network of capacitors 430, may correspond to one of several voltage ramps 521, 522, 523, 524 and 525. As explained above, the slope of each of the voltage ramps 521, 522, 523, 524 and 525 may be expressed as I/C. Therefore, for a given waveform 511 of ion current 405, the higher the capacitance value C of the network of capacitors 430, the smaller the slope of the corresponding voltage ramp may be (e.g., less steep). For example, in FIG. 5, the voltage ramp 521 corresponds to a C value higher than that corresponding to the voltage ramp 522, as the slope 571 of voltage ramp 521 is smaller than the slope 572 of voltage ramp 522. Similarly, the voltage ramp 522 corresponds to a C value higher than that corresponding to the voltage ramp 523, as the slope 572 of voltage ramp 522 is smaller than the slope 573 of voltage ramp 523. Likewise, the voltage ramp 523 corresponds to a C value higher than that corresponding to the voltage ramp 524, as the slope 573 of voltage ramp 523 is smaller than the slope 574 of voltage ramp 524.

FIG. 5 also illustrates a noise floor 501 of value Vmin as well as a saturation threshold 599 of value Vmax, to which the detection circuit 400 may be subject. Vout 415 may be higher than Vmax or lower than Vmin at the end of integrating time 505, and thus may be in an OOR state in which the detection circuit 400 may fail to detect properly. As illustrated in FIG. 5, with integrating time 505 of length T, the waveform 521 may be below Vmin at the end of integration and thus may be in the OOR state. On the other hand, the waveforms 523 and 524 may exceed the saturation threshold 599 of value Vmax at the end of integration, and may also be in the OOR state and thus undetectable. That is, with integrating time 505 set at T, the detection circuit 400 may be able to detect the waveforms 522 and 525 but not the waveforms 521, 523 and 524, which may be out of range and undetectable. Therefore, the network of capacitors 430 may need to be set properly to provide a suitable gain such that the voltage ramp of Vout 415 may be within the detectable range of the device 400 at the end of integrating time 505.

The detectable range of detection device (circuit) 400 is shown in FIG. 5 as the range of Vout above Vmin and below Vmax. It is possible that more than one gain setting of the network of capacitors 430 may be able to result in a voltage ramp of Vout 415 being within the detectable range of detection circuit 400. For example, in FIG. 5, both the waveform 522 having the slope 572 and the waveform 525 having the slope 575 are within the detectable range of detection circuit 400 at the end of integrating time 505, even though the waveform 525 appears to have a higher gain setting of the network of capacitors 430 than the waveform 522, as the slope 575 of waveform 525 is larger than the slope 572 of waveform 522. Although both within the detectable range of detection circuit 400, it is worth noting that the waveform 525 is preferred over the waveform 522, because Vout 415 reaches a higher value at the end of integrating time 505 on the waveform 525 as compared to the waveform 522. Namely, the waveform 525 utilizes a larger portion of the detectable range of detection circuit 400, which makes the subsequent digitization task by the ADC 440 to become easier and more accurate.

A major difference may be readily observed when the detection circuit 400 according to the present disclosure is compared with traditional detection circuit 100, especially when the waveforms of circuit 100 as shown in FIG. 3 are compared with the waveforms of the detection circuit 400 as shown in FIG. 5. In particular, for the detection circuit 100 an indication of the magnitude of ion current 105 resides in the absolute value of Vout 115, whereas for the detection circuit 400 an indication of the magnitude of ion current 405 resides not in the absolute value of Vout 415 but, rather, in the slope of voltage ramp of Vout 415. In some embodiments, the gain setting of the network of capacitors 430 (i.e., a relationship between the slope of voltage ramp Vout 415 and the magnitude of ion current 405) may be calibrated by passing a known current through the detection circuit 400 by using the calibrating module 489 and the test current supplying unit 425. The test current supplying unit 425 includes a source of test current 426 and a changeover switch 427 that is controlled by the calibration module 489. That is, the detection device 400 may be configured to receive a current (test current) of a known magnitude as the ion current 405 by changing the switch 422 and 427 intermittently if necessary, and the calibrating module 489 may analyze the resulted voltage ramp Vout 415 and correlate the slope of the voltage ramp to the magnitude of the known current. The calibration may be performed for each gain setting (i.e., each capacitance configuration) of the network of capacitors 430, and for each gain setting thereof the calibration may be performed for multiple times over which the repeating module 487 may average to result in a more accurate calibration for the respective gain setting.

Various advantages may arise from detecting the slope of voltage ramp of Vout 415 instead of the absolute value of Vout 415. For instance, to move a waveform of Vout 415 out of the OOR state, the detection device 400 may not have to adjust the gain setting C through the network of capacitors 430. Instead, the device 400 may choose to extend or shorten the integrating time Ti to achieve the purpose by the adjusting module 485. As illustrated in FIG. 5, the waveform 521 may ramp slowly due to the ion current 405 being at a very low level. Although the waveform 521 may remain below the noise floor 501 up to integrating time Ti, the waveform 521 may continue to ramp up with time at the slope 571. Even without changing the total capacitance C of the network of capacitors 430 (i.e., without changing gain setting of the integrating circuit 435 of the device 400), given a longer integrating time Ti the waveform 521 may exceed the noise floor 501 (of value Vmin) and thus become detectable by the detection device 400. Namely, an advantage of device 400 lies in a flexibility to trade a longer detection time Ti for a capability of measuring the ion current 451 of a weak value. This is especially advantageous if the gain of the integrating circuit is already at the maximum setting (i.e., the total capacitance C of the network of capacitors 430 is already at the minimum) and there is no way to increase the slope of the Vout waveform by switching to a total capacitance C of a lower value. That is, unlike the detection circuit 100, a noise floor of the detection device 400 may no longer limit how small an ion current 405 may be detected by the device 400 as long as a sufficiently long integrating time Ti is allowed. This flexibility of trading measurement speed for measurement sensitivity is not available in the detection circuit 100. Even under the assumption that the noise floor 501 of the detection device 400 remains the same as the noise floor 301 of the detection circuit 100, the flexibility of the detection device 400 enables it to detect an ion current 405 at a much lower level than can the detection circuit 100, at the expense of a longer detection time. In some embodiments, a detection device 400 may detect an ion current 405 as low as 10 pico-amp (pA) within a detection time of 50 us or so.

The flexibility of trading measurement speed for measurement sensitivity is equally beneficial when an ion current 405 is strong. While the detection circuit 100 of FIG. 1 has a deterministic detection time as disclosed previously, the detection device 400 of FIG. 4 may leverage a stronger ion current 405 for a shorter detection time and thus achieving a faster scan speed of the mass spectrometer 10. For instance, as shown in FIG. 5, it may not need to take the whole length T of integrating time Ti for the analyzing module 482 to determine a slope 573 based on the waveform 523. The analyzing module 482 may determine the slope 573 based on the waveform 523 when an integrating time Ti is shortened to 0.75T or even 0.5T. Namely, samples of Vout 415 of the first three-quarters or even the first half of waveform 523 may be sufficient for the device 400 to determine the slope 573. The reduced integrating time Ti may translate to a 50% or even 100% improvement in the detection speed of the ion current detection process, thereby increasing the measurement efficiency of a mass spectrometer 10 equipped with the detection device 400. The optimizing module 481 may determine to adjust the gain setting of the network of capacitors 430 by the reconfiguring module 484 or an integrating time Ti by the adjusting module 485, or both, Vout 415 may also be reset to ground at the same time through the closing and opening of reset a switch 420 (and in some embodiments, an input switch 422 as well which blocks or allows an ion current 405), so as to provide a clean basis for a new voltage ramp at Vout 415 with the new gain setting of the network of capacitors 430 and/or the new length of integrating time Ti.

Another significant benefit of detecting the slope rather than the absolute value of Vout 415 is manifested in a better immunity toward error sources such as offsets in the detection device 400. For instance, both detection circuits 100 and 400 may be subjected to certain amount of DC offset error. A DC offset voltage presented in the circuit 100 may cause an erroneous reading in measuring the ion current 105, whereas the same DC offset voltage may not cause an error in measuring the ion current 405. As illustrated in FIG. 3, a DC offset voltage Vos presented at the output terminal of op-amp 110 may shift the waveform 323 to a waveform 3231, causing the representative value of Vout 115 to shift from v3 to (v3+Vos). Assuming the detection circuit 100 has a 10% Vos in the positive direction (i.e., Vos=0.1·v3), the measured ion current 105 would thus be 10% higher than what it actually is, which translates to a 10% error in the relative concentration of the corresponding ions in the specimen under test. For the detection device 400, however, a DC offset voltage Vos may not change the slope of waveform of Vout 415 and not cause an error in the measurement of ion current 405. As illustrated in FIG. 5, a DC offset voltage 5531 (of value Vos) presented at the output terminal 402 of op-amp 410 may shift the waveform 523 to a waveform 5231. Nevertheless, a slope 5731 of waveform 5231 remains substantially the same as the slope 573 of waveform 523. Therefore, no error in the measurement is induced by the DC offset voltage 5531 of the detection device 400.

As the analog voltage ramp of Vout 415 is digitized by ADC 440 before being analyzed by the processor 460, various techniques may be performed in digital domain to further strengthen the immunity of the detection device 400 to practical imperfections. FIG. 6 depicts a set of waveforms similar to those shown in FIG. 5, but with more practical details included. Compared with the ion current waveform 511, an ion current waveform 611 includes some fluctuations which may be resulted from capacitive couplings from various high-voltage, high-power or high-frequency sources within a mass spectrometer. Consequently, according to the governing equation of Vout=I·Ti/C (wherein I represents a magnitude of ion current 405, Ti represents a length of integrating time, and C represents the total capacitance of the network of capacitors 430), Vout waveforms 621, 622, 623 and 624 may also include some fluctuations corresponding to the fluctuations in the current waveform 611, with each of the waveforms 621, 622, 623 and 624 corresponding to a different gain setting of the network of capacitors 430. Take a voltage ramp 624 for an example. Although the digitized samples of waveform 624 may also include fluctuations therein, the fluctuations may be reduced or otherwise removed to the first order by one or more stages of digital filter 450 that follows ADC 440. The module 482a of the analyzing module 482 may process the filtered digital samples output from the digital filter 450 to further reduce more non-idealities therein, resulting in a first order fitting line 664 that best approximates the waveform 624 of voltage ramp at Vout 415. A slope 674 of first order fitting line 664 is then determined by the module 482b of the analyzing module 482 and designated as the slope of waveform 624, which in turn serves as an indication of an abundance of ion or molecule having a specific m/z in a specimen being analyzed by the mass spectrometer.

In some embodiments, the measurement of a voltage ramp for a specific gain setting of the network of capacitors 430, such as each of waveforms 621, 622, 623 and 624, may be repeated for several times by the repeating module 487, over which the analyzing module 482 may average to result in a more accurate voltage ramp of Vout 415 and thus a more accurate determination of the slope of the voltage ramp. The averaging over the multiple ramps effectively improve the signal-to-noise ratio of the resulted ion current waveform. For example, without changing the gain setting of the network of capacitors 430, the detection device 400 may reset (through turning on reset switch 420) to bring Vout 415 to zero, turn off reset switch 420 to capture the voltage ramp of Vout 415 for the first time, reset again to bring Vout 415 back to zero, capture the voltage ramp of Vout 415 for the second time, reset again to bring Vout 415 back to zero again, and capture the voltage ramp of Vout 415 for the third time. The Analyzing module 482 may then receive from ADC 440 the samples of the three ramps (which may or may not pass FIR 450) and average over the samples of the three ramps to achieve a more a more accurate voltage ramp of Vout 415 as well as a more accurate determination of the slope of the voltage ramp.

As disclosed earlier, in some embodiments, one or more large peaks or valleys, or both, may be resulted in the ion current when a QMF of a mass spectrometer is adjusted from passing ions of a specific value of m/z to passing ions of a different value of m/z. The phenomenon has been shown in FIG. 2 as applied to the detection circuit 100 of FIG. 1. The detection circuit 100 deals with this large transient perturbation to the ion current by waiting until the transient perturbation dies down. As a result, a significantly long waiting period, such as waiting periods 234 and 232, are wasted in the detection process.

In contrast, the detection device 400 may have the advantage to utilize a Vout waveform during the large transient perturbation to predict a slope of a first-order fitting curve that may best fit the Vout waveform after the transient perturbation has settled. FIG. 7 shows an ion current waveform 714 that is identical to the ion current waveform of 214 in FIG. 2. FIG. 7 also shows a Vout waveform 724 resulted from an ion current waveform 714 being applied to the detection device 400. It may take a time period 734 for the ion current 714 to settle. A first-order fitting line 764 may best fit the Vout waveform 724 after time t1, when the large transient perturbation between times t0 and t1 have settled. With advanced algorithms and complicated digital filtering, the analyzing module 482 may predict or otherwise extrapolate and approximate a slope 774 based on the Vout waveform 724 during the time period 734. That is, it is not necessary for the detection device 400 to wait for the passage of time period 734 before obtaining a reasonably acceptable estimate of slope 774. The slope 774 estimated or approximated in this way may not be as accurate as relying on the Vout waveform 724 solely after time t1, but it may give a reasonably close result which is especially beneficial when the detection result of a specimen needs to be provided promptly with no time t0 wait for the settling of Vout after each scan of QMF.

In addition to primary reasons presented above, the detection device 400 may possess at least the following secondary reasons for realizing a high-speed low-noise ion current detection circuit in a mass spectrometer as compared to the circuit 100. Firstly, gain settings of the device 400 may be realized by the capacitors network and low impedance range switches, while gain settings of detection circuit 100 are realized by high-value resistors. High-value resistors are inherent noise sources, while capacitors may provide inherent noise filtering. Therefore, the detection device 400 is intrinsically a low-noise design as compared to the detection circuit 100. Secondly, due to sensitivity of offset, the detection circuit 100 requires op-amp 110 to have a very high open-loop gain. An op-amp of high open-loop gain is often prone to pick up noise, and also suffers from slow recovery once the op-amp enters saturation. In contrast, op-amp 410 used in the device 400 may not require a high open-loop gain, as the slope of Vout 415 is not sensitive to a DC offset voltage. Therefore, the op-amp 410 may be less prone to pick up noise, and the recovery from saturation may be faster. Thirdly, the noise floor 501 of FIG. 5 is inherently much lower than the noise floor 301 of FIG. 3. The much-lower noise floor 501 enables the use of various signal processing/digital filtering techniques to reduce unwanted signals and random noise in digital domain. The detection circuit 100, due to a much higher noise floor 301, may not be able to leverage digital filtering or other signal processing techniques to reduce and filter out unwanted signals.

FIG. 8 illustrates an example process 800 for detecting a current in a system in accordance with the present disclosure. In FIG. 8 depicts an example of process 800 for detecting an ion current in a mass specification. The process 800 may include one or more operations, actions, or functions shown as blocks such as 810, 820, 830, 840, 850 and 860. Although illustrated as discrete blocks, various blocks of process 800 may be divided into additional blocks, combined into fewer blocks, or eliminated, depending on the desired implementation. The process 800 may be implemented by the ion current detection device 400. The process 800 may begin with a block 810.

At 810, the process 800 may involve the integrating circuit 435 of the detection device 400 converting an ion current 405 into a voltage signal 415 showing voltage ramp in analog domain. The integrating circuit 435 may include the op-amp 410, reset the switch 420 and the network of capacitors 430 as shown in FIG. 4. The step of converting 810 may happen over a length of integrating time Ti. The ion current 405 may have a waveform 611 of FIG. 6, and Vout 415 may have a waveform 621, 622, 623 or 624, depending on a gain setting of the network of capacitors 430. The block 810 may be followed by a block 820.

At 820, the process 800 may involve an ADC digitizing the voltage ramp of Vout 415 from analog domain into voltage samples in digital domain. The ADC may be ADC 440 of the device 400 in FIG. 4. The digitized voltage samples may be an equivalent representation of the voltage ramp of Vout 415 in analog domain. The Block 820 may be followed by a block 830.

At 830, the process 800 may involve one or more digital filters connected in series to remove or otherwise reduce unwanted noise and/or other nonlinear components from the digital voltage samples. The one or more digital filters may include one or more stages of digital filter 450 of the device 400 as shown in FIG. 4. The Block 830 may be followed by a block 840.

At 840, the process 800 may involve a processor analyzing the digital samples that pass the one or more digital filters. The processor may be a processor 460 of FIG. 4. According to the analysis of the determining module 483 implemented in the processor 460, the process 800 may determine whether the voltage ramp converted from the ion current 405 by the integrating circuit 435 is out of a detection range (OOR) of process 800. For example, for Vout 415 having a waveform 621 as shown in FIG. 6, in the process 800, the determining module 483 may determine Vout 415 is out of range (OOR) since Vout 415 has a value below the noise floor 601 at the end of integrating time Ti. As another example, for Vout 415 having a waveform 623 as shown in FIG. 6, the determining module 483 may determine Vout 415 is out of range (OOR) since Vout 415 has a value above the saturation threshold 699 at the end of integrating time Ti. On the other hand, for Vout 415 having a waveform 622 as shown in FIG. 6, the determining module 483 may determine Vout 415 is not out of range since Vout 415 has a value between the noise floor 601 and the saturation threshold 699 at the end of integrating time Ti. At 840, the determining module 483 may predicts the OOR state based on the voltage ramp and a predetermined detectable range prior to the end of integrating time Ti for time saving. In the process 800, If the determining module 483 determines the voltage ramp converted from the ion current 405 by the integrating circuit 435 is OOR, the process 800 may accordingly determine an OOR state to be positive. Otherwise, the process 800 may determine an OOR state to be negative. The block 840 may be followed by a block 850 in response to the determining of a positive OOR state. Alternatively, the block 840 may be followed by a block 860 in response to the determining of a negative OOR state.

At 850, the process 800 may involve a reconfiguring the network capacitors 430 to adjusting the gain setting of the integrating circuit 435. At 850, the reconfiguring module 484 may adjust a total capacitance of the network of capacitors 430 of the device 400. Alternatively or additionally, the process 800 may involve an adjusting the length if the integration time Ti over which the ion current 405 is converted to the voltage ramp Vout. For example, the adjusting module 485 may reduce the integration time Ti from T to 0.75 T for voltage ramp 415 having a waveform 623. The block 850 may be followed by a block 810.

At 860, the process 800 may involve analyzing the digitized voltage samples of the analog voltage to determine the slope of the voltage ramp. The analyzing module 482 may determine a first-order fitting line that best represents the digitized voltage samples of the analog voltage ramp and designate a slope of the first-order fitting line as the slope of the analog voltage ramp. For example, the analyzing module 482 determines first-order fitting line 662 that best fits a voltage ramp waveform 622, and designates the slope 672 of first-order fitting line 662 as the slope of waveform 622. The slope 672 thus may represent the magnitude of ion current 405. The process 800 may include a determining a magnitude of the current 405 based on the slope of the voltage ramp and the gain setting, and may be interpreted as an indication of an abundance of ion or molecule having a specific m/z in a specimen being analyzed by the mass spectrometer. The process 800 may end at the block 860.

FIG. 9 illustrates an example method (process) 900 for detecting a current from the sensor 490 using the device 400. If the method 900 has been started, at step 910, the switching module 486 may set the reset switch 420 and the input switch 422. Firstly, the input switch 422 may be turned off and to block the current 405 and the reset switch 420 may be turned on to reset the network of capacitors 430, then the reset switch 420 may be turned off to start integrating and the input switch 422 may be turned on to pass the current 405 to be converted to the voltage ramp by the integrating circuit 435. At step 912, the analyzing module 482 may analyze the plurality of voltage samples to determine the slope of the voltage ramp described with the process 800 in FIG. 8. At step 913, during the analyzing or after the analyzing, if the OOR state is determined or predicted by the determining module 483, at step 915, the switching module 486 may turns off the reset switch 420 to reconfigure the network of capacitors 430 for reconverting to the voltage ramp.

Even if the OOR state is not found at step 913, at step 914, the optimizing module 481 may check the states or conditions of the determined slope, the integrating time Ti and the like from the view point of measurement speed, measurement sensitivity, and measurement accuracy. When the determined slope is not so large (sharp, high-angle) and a larger slope may be selectable based on the saturation threshold 599 or 699, changing a gain of the network of capacitors to select a larger slope is beneficial to minimize the integrating time Ti, that may reduce the detection time of the device 400 especially when the repeating measurement is selected. On the other hand, when the measurement accuracy is required rather than the speed, and if the determined slope is not so small and a smaller (lower angle) slope may be selectable based on the noise floor 501 or 601, changing a gain of the network of capacitors to select a smaller slope is beneficial to increase the accuracy.

From the view point of the OOR state and/or the optimizing requirement, at step 920, if reconfiguring the network of capacitors 430 is required to change a gain, at step 925, the reconfiguring module 484 reconfigures the network of capacitors 430 to set an appropriate gain to adjust the length of integration time Ti to improve a detection speed or a detection accuracy. Also, from the view point of the OOR state and/or the optimizing requirement, and according to the gain of the network of capacitors that was set at the step 925, at step 930, if adjusting of the integrating time Ti is required, at step 935, the adjusting module 485 may adjust the length of integration time Ti according to the OOR state, the optimizing requirement and/or a gain of the reconfigured network of capacitors 430.

Then, at step 950, when calibration is required, at step 955, the calibrating module 489 may calibrate the gain setting of the integrating circuit 435 by sending a calibrating current (test current) of known value to the integrating circuit 435 using the current supplying circuit 425. The calibrating module 489 may record the slope of the voltage ramp resulted from the test current to correct or compensate a measured ion current 405 with the gain setting.

When the OOR state is not observed and the optimization is not required, at step 960, requirement of repeating of measurement is judged. If the repeating is required, the repeating module 487 may repeat converting of the ion current 405 to the voltage ramp for multiple times. The number of repetitions may be determined in advance. The plurality of voltage samples comprises multiple sets of voltage samples and, during the repetitions, at step 912, the analyzing module 482 may analyze the multiple sets of voltage samples to determine the slope of the voltage ramp by averaging over the multiple sets of voltage samples. At the step 970, the outputting module 488 may determine a magnitude of the ion current 405 based on the slope of the voltage ramp and the gain setting and output the magnitude of the ion current 405 via a communication means such as wired or wireless communication including Wi-Fi connection, wireless LAN, cellular data connection, Bluetooth® or the like.

FIG. 10 depicts an example of a system that includes a sensor configured to generate a current signal 405 to be interpreted and the device 400 for detecting the current signal 405. The system shown in FIG. 10 is a miniaturized mass spectrometer 90 that may include an ion current detection circuit similar to the device 400 of FIG. 4 to detect the ion current 405 to sense a part of a plurality of gas ions filtered by mass to charge ratios (m/z). The mass spectrometer 90 may include an ion drive 91. The ion drive 91 may include one or more filament heaters that may emit electrons when heated up by a filament current flowing through each of the filament heaters. The filament current is maintained with a high accuracy to minimize fluctuations in number of electrons emitted from the filament. The mass spectrometer 90 may also include an array of acceleration electrodes 92. The acceleration electrodes 92 may be used to guide and accelerate charged particles in the mass spectrometer 90. Electrons emitted from the ion drive 91 may be accelerated by the acceleration electrodes 92, forming a high-speed electron flow 95 that flows toward an opposite end of mass spectrometer 90. The high-speed electron flow 95 may encounter specimen gas molecules 96 and ionize gas molecules 96 into an ion flow 97 having ionized gas molecules.

The ion flow 97 may be further accelerated and guided by the acceleration electrodes 92 to move toward a mass filter 93. The mass filter 93 may be a QMF. The QMF 93 may select to pass a portion of the ionized gas molecules 96 in the ion flow 97, or selected ions 98, having a specific m/z value or a specific atomic mass unit (AMU). The selected ions 98 that pass the QMF 93 may subsequently be sensed or otherwise collected by an ion sensing device 99 (490) and formed into the ion current 405 that flows into an input terminal of the ion current detection device 400. The ion sensing device 95 may be embodied using various mechanisms, or a combination thereof. For example, the ion sensing device 95 may be a Faraday cup, an ion trap, an electron multiplier, or a hybrid Faraday cup/electron multiplier. In some embodiment, a mass spectrometer 90 may also include an enclosure 94 in which an ion drive 91, QMF 93, an ion sensing device 95 and an ion current detection circuit 400 are enclosed. The enclosure 94 may be generally cylindrical in shape. Alternatively, the enclosure 94 may be generally elliptical in shape or in another suitable shape.

FIG. 11 depicts another example of a system that includes a sensor configured to generate a current signal 405. The system shown in FIG. 11 is a miniaturized spectrometer (optical spectrometer) 80 that may include an optical current detection circuit similar to the device 400 of FIG. 4 to detect the optical current 405 to measure properties of light over a specific portion of the electromagnetic spectrum. The variable measured may be the light's intensity. The independent variable may be the wavelength of the light or a unit directly proportional to the photon energy, such as reciprocal centimeters or electron volts, which has a reciprocal relationship to wavelength. Spectrometers may also operate over a wide range of non-optical wavelengths, from gamma rays and X-rays into the far infrared.

A system 80 shown in FIG. 11 is a Raman spectroscopy system, especially a CARS (Coherent Anti-Stokes Raman Scattering) spectroscopy system 80 that may include a laser unit for emitting a Stokes light (Stokes beam) and a Pump light (Pump beam) 87 to a sample 89 such as a human body, and a detection unit 82 to detect a CARS light 88 from the sample 89. The detection unit 82 may include a spectroscope 83 such as a grating, an optical detector 84 (490) such as a photo diode or CCD to generate an optical current 405, and a detection device 400.

The present disclosure provides novel methods and circuits for detecting a current of a system such as a mass spectrometer and other type of spectrometers. Compared with traditional current detection circuits, the present disclosure provides means for realizing high-speed and low-noise detection for the sensed current. The improved current detection scheme according to the present disclosure is able to greatly improve performances of the spectrometers and other systems equipped with sensor or sensors.

In this specification, methods and circuits for detecting an ion current in a mass spectrometer are described. A circuit and a method may involve converting, over a length of integration time, the ion current to a voltage ramp by an integrating circuit having a gain setting. The circuit and the method may also involve determining a slope of the voltage ramp. The circuit and the method may also involve determining a magnitude of the ion current based on the slope of the voltage ramp and the gain setting. The circuit and the method may further involves determining an out-of-range state based on the voltage ramp and adjusting the gain setting of the integrating circuit, or the length of integration time or both, in response to the determining of the out-of-range state One of the aspect of the above is a method of detecting an ion current in a mass spectrometer. The method comprises: (i) converting, over a length of integration time, the ion current to a voltage ramp by an integrating circuit having a gain setting; (ii) determining a slope of the voltage ramp; and (iii) determining a magnitude of the ion current based on the slope of the voltage ramp and the gain setting. The step of determining a slope of the voltage ramp may include (a) digitizing, by an analog-to-digital converter (ADC), the voltage ramp into a plurality of voltage samples, the plurality of voltage samples representing the voltage ramp; and (b) analyzing, by a processor, the plurality of voltage samples to determine the slope of the voltage ramp. The analyzing of the plurality of voltage samples to determine the slope of the voltage ramp may comprise determining a first-order fitting line based on the plurality of voltage samples; and designating a slope of the first-order fitting line as the slope of the voltage ramp.

The method may further comprise reducing, by one or more digital filters coupled in series, a noise component of the plurality of voltage samples before analyzing the plurality of voltage samples. The method may further comprise: determining an out-of-range (OOR) state based on the voltage ramp and a predetermined detectable range; and adjusting the gain setting of the integrating circuit, the length of integration time, or both, in response to the determining of the OOR state such that the voltage ramp is within the predetermined detectable range at an end time of the length of integration time. The method may further comprise repeating the converting of the ion current to the voltage ramp for multiple times. The plurality of voltage samples may comprise multiple sets of voltage samples resulted from the repeating, and the analyzing of the plurality of voltage samples to determine the slope of the voltage ramp may comprise averaging over the multiple sets of voltage samples. The method may further comprise calibrating the gain setting of the integrating circuit by sending a calibrating current of a known value to the integrating circuit and recording the slope of the voltage ramp resulted from the calibrating current.

In another aspect of the above is a circuit of detecting an ion current and implementable to a mass spectrometer. The circuit comprises: an integrating circuit having a gain setting and configured to convert the ion current to a voltage ramp over a length of integration time; an analog-to-digital converter (ADC) configured to digitize the voltage ramp into a plurality of voltage samples; and a processor configured to determine a slope of the voltage ramp based on one or more voltage samples of the plurality of voltage samples and further configured to determine a magnitude of the ion current based on the slope of the voltage ramp and the gain setting. The circuit may further comprise one or more digital filters configured to reduce a noise component of the plurality of voltage samples and generate the one or more voltage samples of the plurality of voltage samples.

The integrating circuit may comprise (i) an operational amplifier (op-amp) having an inverting terminal as an input terminal, a non-inverting terminal connected to a reference voltage as a ground terminal, and an output terminal, the input terminal configured to receive the ion current; (ii) a reset switch connected between the input terminal and the output terminal of the op-amp, the reset switch configured to short-circuit the output terminal of the op-amp to the input terminal of the op-amp when the reset switch is turned on; and (iii) a variable relay connected between the input terminal and the output terminal of the op-amp, the variable relay configured to provide the gain setting of the integrating circuit. The variable relay may include a plurality of capacitors; and a plurality of range switches, each of the plurality of range switches connected to at least one of the plurality of capacitors. The plurality of range switches are configured to connect one or more capacitors of the plurality of capacitors to provide the gain setting of the integrating circuit. The plurality of range switches are further configured to connect one or more capacitors of the plurality of capacitors in series, in parallel, or both in series and in parallel, to adjust the gain setting of the integrating circuit.

The processor may be further configured to determine an out-of-range (OOR) state based on the voltage ramp and a predetermined detectable range. The processor may be further configured to adjust the gain setting of the integrating circuit and reset the voltage ramp via the reset switch according to the OOR state. The processor may be further configured to determine an out-of-range (OOR) state based on the voltage ramp and a predetermined detectable range, and wherein the processor is further configured to reset the voltage ramp via the reset switch and adjust the length of integration time according to the OOR state. The integrating circuit may further comprise an input switch configured to pass the ion current while the ion current is converted to the voltage ramp, and further configured to block the ion current while the reset switch is turned on to reset the voltage ramp.

In this specification, a miniaturized mass spectrometer for analyzing gas molecules is disclosed. The mass spectrometer comprises (i) an ion drive configured to ionize the gas molecules into an ion flow comprising a plurality of gas ions having a plurality of values of atomic mass unit (AMU); (ii) a quadrupole mass filter (QMF) configured to selectively pass a first part of the plurality of gas ions, each gas ion of the first part of the plurality of gas ions having a first value of AMU; (iii) an ion sensing device configured to sense the first part of the plurality of gas ions and generate a first ion current; and (iv) an ion current detection circuit configured to detect the first ion current. The ion current detection circuit may comprise: an integrating circuit having a gain setting and configured to convert the first ion current to a voltage ramp over a length of integration time; an analog-to-digital converter (ADC) configured to digitize the voltage ramp into a plurality of voltage samples; and a processor configured to determine a slope of the voltage ramp based on one or more voltage samples of the plurality of voltage samples and further configured to determine a magnitude of the first ion current based on the slope of the voltage ramp and the gain setting.

The ion drive may comprise a filament heater configured to generate a plurality of electrons; and one or more acceleration electrodes configured to accelerate the plurality of electrons to form a high velocity electron flow that ionize the gas molecules into the ion flow. The ion current detection circuit may further comprise one or more digital filters configured to reduce a noise component of the plurality of voltage samples and generate the one or more voltage samples of the plurality of voltage samples. The integrating circuit may comprise an operational amplifier (op-amp) having an inverting terminal as an input terminal, a non-inverting terminal connected to a reference voltage as a ground terminal, and an output terminal, the input terminal configured to receive the first ion current; a reset switch connected between the input terminal and the output terminal of the op-amp, the reset switch configured to short-circuit the output terminal of the op-amp to the input terminal of the op-amp when the reset switch is turned on; and a variable relay connected between the input terminal and the output terminal of the op-amp, the variable relay configured to provide the gain setting of the integrating circuit. The variable relay may comprise: a plurality of capacitors; and a plurality of range switches, each of the plurality of range switches connected to at least one of the plurality of capacitors. The plurality of range switches are configured to connect one or more capacitors of the plurality of capacitors to provide the gain setting of the integrating circuit. The plurality of range switches may be further configured to connect one or more capacitors of the plurality of capacitors in series, in parallel, or both in series and in parallel, to adjust the gain setting of the integrating circuit.

The processor may be further configured to determine an out-of-range (OOR) state based on the voltage ramp and a predetermined detectable range. The processor may be further configured to adjust the gain setting of the integrating circuit, the length of integration time, or both, according to the OOR state such that the voltage ramp is within the predetermined detectable range at an end time of the length of integration time. The ion sensing device may comprise a Faraday cup, an ion trap, an electron multiplier, or a combination of two or more thereof.

The articles "a" and "an" are used herein to refer to one or to more than one (i.e., to at least one) of the grammatical object of the article. By way of example, "a user" means one user or more than one users. Reference throughout this specification to "one embodiment," "an embodiment," "one example," or "an example" means that a particular feature, structure, or characteristic described in connection with the embodiment or example is included in at least one embodiment of the present disclosure. Thus, appearances of the phrases "in one embodiment," "in an embodiment," "one example," or "an example" in various places throughout this specification are not necessarily all referring to the same embodiment or example. Furthermore, the particular features, structures, databases, or characteristics may be combined in any suitable combinations and/or sub-combinations in one or more embodiments or examples. In addition, it should be appreciated that the figures provided herewith are for explanation purposes to persons ordinarily skilled in the art and that the drawings are not necessarily drawn to scale.

Embodiments in accordance with the present disclosure may be embodied as an apparatus, method, or computer program product. Accordingly, the present disclosure may take the form of an entirely hardware-comprised embodiment, an entirely software-comprised embodiment (including firmware, resident software, micro-code or the like), or an embodiment combining software and hardware aspects that may all generally be referred to herein as a "circuit," "module," or "system." Furthermore, embodiments of the present disclosure may take the form of a computer program product embodied in any tangible medium of expression having computer-usable program code embodied in the medium.

The flow diagrams and block diagrams in the attached figures illustrate the architecture, functionality, and operation of possible implementations of systems, methods, and computer program products according to various embodiments of the present disclosure. In this regard, each block in the flow diagrams or block diagrams may represent a module, segment, or portion of code, which comprises one or more executable instructions for implementing the specified logical function(s). It will also be noted that each block of the block diagrams and/or flow diagrams, and combinations of blocks in the block diagrams and/or flow diagrams, may be implemented by special purpose hardware-based systems that perform the specified functions or acts, or combinations of special purpose hardware and computer instructions. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flow diagram and/or block diagram block or blocks.

Although the present disclosure is described in terms of certain embodiments, other embodiments will be apparent to those of ordinary skill in the art, given the benefit of this disclosure, including embodiments that do not provide all of the benefits and features set forth herein, which are also within the scope of this disclosure. It is to be understood that other embodiments may be utilized, without departing from the scope of the present disclosure.

The invention claimed is:

1. A device of detecting a current from a sensor, the device comprising:
an integrating circuit including a network of capacitors for providing a gain setting and configured to convert the current to a voltage ramp over a length of integration time, the integrating circuit further including a reset switch configured to connect an input and an output of the network of capacitors when the reset switch is turned on;
an analog-to-digital converter (ADC) configured to digitize the voltage ramp into a plurality of voltage samples; and
a processor that is configured to execute a set of modules, wherein
the set of modules includes:
an analyzing module that is configured to analyze the plurality of voltage samples to determine a slope of the voltage ramp;
an outputting module that is configured to determine a magnitude of the current based on the slope of the voltage ramp and the gain setting;
a determining module that is configured to determine an out-of-range (OOR) state based on the voltage ramp; and
a reconfiguring module that is configured to reconfigure the network of capacitors according to the OOR state and reset the voltage ramp via the reset switch, and
the OOR state includes values below a noise floor and above a saturation threshold, wherein the noise floor is a minimum detectable level of the detection circuit.

2. The device according to claim 1, wherein the determining module predicts the OOR state based on the voltage ramp and a predetermined detectable range.

3. The device according to claim 1, wherein the set of modules further includes an adjusting module configured to adjust the length of integration time according to the OOR state.

4. The device according to claim 1, wherein the reconfiguring module reconfigures the network of capacitors and adjusts the length of integration time to improve a detection speed or a detection accuracy.

5. The device according to claim 1, wherein the analyzing module includes a module configured to determine a first-order fitting line based on the plurality of voltage samples, and
a module configured to designate a slope of the first-order fitting line as the slope of the voltage ramp.

6. The device according to claim 1, wherein the integrating circuit further includes an input switch configured to on and off the current to the network of capacitors, and
wherein the set of modules further includes a switch controlling module that is configured to control the input switch to pass the current while the current is converted to the voltage ramp and to block the current while the reset switch is turned on to reset the voltage ramp.

7. The device according to claim 1, wherein the set of modules further includes a repeating module that is configured to repeat converting of the current to the voltage ramp for multiple times, wherein the plurality of voltage samples comprise multiple sets of voltage samples resulted from the repeating, and the analyzing modules determines the slope of the voltage ramp by averaging over the multiple sets of voltage samples.

8. The device according to claim 1, wherein the set of modules further includes a calibrating module that is configured to calibrate the gain setting of the integrating circuit by sending a calibrating current of a known value to the integrating circuit and recording the slope of the voltage ramp resulted from the calibrating current.

9. The device according to claim 1, further comprising:
one or more digital filters configured to reduce a noise component of the plurality of voltage samples and generate the one or more voltage samples of the plurality of voltage samples.

10. A mass spectrometer that includes:
an ion drive configured to ionize gas molecules into an ion flow comprising a plurality of gas ions having a plurality of values of atomic mass unit (AMU);
a mass filter configured to selectively pass a first part of the plurality of gas ions, each gas ion of the first part of the plurality of gas ions having a first value of AMU;
an ion sensor configured to sense the first part of the plurality of gas ions and generate a first ion current; and
the device according to claim 1 that detects the first ion current.

11. An optical spectrometer that includes:
an optical sensor configured to measure properties of light over a specific portion of the electromagnetic spectrum and generate a first optical current; and
the device according to claim 1 that detects the first optical current.

12. A system that includes:
a sensor configured to generate a current signal to be interpreted; and
the device according to claim 1 that detects the current signal.

13. A method of detecting a current from a sensor using a device, wherein the device includes an integrating circuit including a network of capacitors for providing a gain setting and a reset switch for connecting an input and an output of the network of capacitors, an analog-to-digital converter (ADC), and a processor,
wherein the method includes:
converting, over a length of integration time, the current to a voltage ramp by the integrating circuit having a gain setting;
digitizing, by the ADC, the voltage ramp into a plurality of voltage samples, the plurality of voltage samples representing the voltage ramp;
analyzing, by the processor, the plurality of voltage samples to determine the slope of the voltage ramp;
determining a magnitude of the current based on the slope of the voltage ramp and the gain setting
determining an out-of-range (OOR) state based on the voltage ramp; and
reconfiguring the network of capacitors according to the OOR state and resetting the voltage ramp via the reset switch, and
the OOR state includes values below a noise floor and above a saturation threshold, wherein the noise floor is a minimum detectable level of the detection circuit.

14. The method according to claim 13, wherein the determining the OOR state includes predicting the OOR state based on the voltage ramp and a predetermined detectable range.

15. The method according to claim 13, further including adjusting the length of integration time according to the OOR state.

16. The method according to claim 13, wherein the reconfiguring includes reconfiguring the network of capacitors and adjusts the length of integration time to improve a detection speed or a detection accuracy.

17. The method according to claim 13, wherein the analyzing comprises:
determining a first-order fitting line based on the plurality of voltage samples; and
designating a slope of the first-order fitting line as the slope of the voltage ramp.

18. The method according to claim 13, wherein the integrating circuit further includes an input switch configured to on and off the current to the network of capacitors, and
wherein the method further includes switching the input switch to pass the current while the current is converted to the voltage ramp and to block the current while the reset switch is turned on to reset the voltage ramp.

19. The method according to claim 13, further including repeating converting of the current to the voltage ramp for multiple times, wherein the plurality of voltage samples comprises multiple sets of voltage samples and determining the slope of the voltage ramp by averaging over the multiple sets of voltage samples.

20. A nontransitory computer readable medium including a program product for a computer to operate a system including a spectrometer, the spectrometer including a sensor and a device configured to detect a current from the sensor, wherein the device includes:
an integrating circuit including a network of capacitors for providing a gain setting and configured to convert the current to a voltage ramp over a length of integration time, the integrating circuit further including a reset switch configured to connect an input and an output of the network of capacitors when the reset switch is turned on; and
an analog-to-digital converter (ADC) configured to digitize the voltage ramp into a plurality of voltage samples, and
wherein the computer program includes executable codes for performing steps of:
analyzing the plurality of voltage samples to determine a slope of the voltage ramp;
determining a magnitude of the current based on the slope of the voltage ramp and the gain setting
determining an out-of-range (OOR) state based on the voltage ramp; and
reconfiguring the network of capacitors according to the OOR state and resetting the voltage ramp via the reset switch based on the slope of the voltage ramp, and
the OOR state includes values below an noise floor and above a saturation threshold, wherein the noise floor is a minimum detectable level of the detection circuit.

* * * * *